(12) United States Patent
Reddy et al.

(10) Patent No.: US 10,850,067 B2
(45) Date of Patent: Dec. 1, 2020

(54) IMPLANTATION OF AN ACTIVE MEDICAL DEVICE USING THE INTERCOSTAL VEIN

(71) Applicant: CARDIAC PACEMAKERS, INC., St. Paul, MN (US)

(72) Inventors: G. Shantanu Reddy, Minneapolis, MN (US); Peter Hall, Andover, MN (US); Andrew L. De Kock, Ham Lake, MN (US); Christopher Alan Fuhs, Roseville, MN (US); Daniel J. Foster, Lino Lakes, MN (US); James K. Cawthra, Jr., Ramsey, MN (US)

(73) Assignee: CARDIAC PACEMAKERS, INC., St. Paul, MN (US)

(*) Notice: Subject to any disclaimer, the term of this patent is extended or adjusted under 35 U.S.C. 154(b) by 301 days.

(21) Appl. No.: 15/846,081

(22) Filed: Dec. 18, 2017

(65) Prior Publication Data
US 2018/0169384 A1    Jun. 21, 2018

Related U.S. Application Data

(60) Provisional application No. 62/437,063, filed on Dec. 21, 2016.

(51) Int. Cl.
| | |
|---|---|
| *A61N 1/39* | (2006.01) |
| *A61M 25/01* | (2006.01) |
| *A61N 1/05* | (2006.01) |
| *A61B 5/00* | (2006.01) |

(Continued)

(52) U.S. Cl.
CPC ....... *A61M 25/0133* (2013.01); *A61B 5/0422* (2013.01); *A61B 5/0538* (2013.01); *A61B 5/6851* (2013.01); *A61B 5/6876* (2013.01); *A61N 1/0563* (2013.01); *A61N 1/0587* (2013.01); *A61N 1/3956* (2013.01); *A61B 5/4836* (2013.01); *A61B 5/686* (2013.01)

(58) Field of Classification Search
CPC .... A61B 5/6876; A61N 1/0587; A61N 1/056; A61N 1/0563
See application file for complete search history.

(56) References Cited

U.S. PATENT DOCUMENTS

| | | |
|---|---|---|
| 5,331,966 A | 7/1994 | Bennett et al. |
| 6,647,292 B1 | 11/2003 | Bardy et al. |
| 6,721,597 B1 | 4/2004 | Bardy et al. |

(Continued)

FOREIGN PATENT DOCUMENTS

| | | |
|---|---|---|
| WO | 2016148928 A1 | 9/2016 |
| WO | 2016149262 A1 | 9/2016 |

OTHER PUBLICATIONS

Moeinipour et al., "A Rare Central Venous Catheter Malposition: A Case Report," Anesth Pain Med., 4(1): 1-3, Feb. 5, 2014.

(Continued)

*Primary Examiner* — George R Evanisko
(74) *Attorney, Agent, or Firm* — Seager, Tufte & Wickhem LLP

(57) ABSTRACT

Implantation of a cardiac stimulus system using the ITV. Access to the ITV may be performed using the intercostal vein as an access point, and entering the ITV through an ostium therebetween. The intercostal vein may be located on a costal groove on an inferior portion of a rib. Advancement from the intercostal vein to the ITV may then be performed in a superior direction, an inferior direction, or both.

20 Claims, 21 Drawing Sheets

(51) Int. Cl.
  *A61B 5/053*  (2006.01)
  *A61B 5/042*  (2006.01)

(56) References Cited

U.S. PATENT DOCUMENTS

| | | |
|---|---|---|
| 7,149,575 B2 | 12/2006 | Ostroff et al. |
| 7,655,014 B2 | 2/2010 | Ko et al. |
| 7,783,340 B2 | 8/2010 | Sanghera et al. |
| 7,818,068 B2 | 10/2010 | Meadows et al. |
| 7,962,222 B2 | 6/2011 | He et al. |
| 8,005,543 B2 | 8/2011 | Libbus et al. |
| 8,157,813 B2 | 4/2012 | Ko et al. |
| 8,386,048 B2 | 2/2013 | McClure et al. |
| 8,483,843 B2 | 7/2013 | Sanghera et al. |
| 8,543,216 B2 | 9/2013 | Carbunaru et al. |
| 2005/0043765 A1 | 2/2005 | Williams et al. |
| 2012/0029335 A1 | 2/2012 | Sudam et al. |
| 2015/0025612 A1 | 2/2015 | Haasl et al. |
| 2015/0051610 A1 | 2/2015 | Schmidt et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0224320 A1 | 8/2015 | Stahmann |
| 2015/0297902 A1 | 10/2015 | Stahmann et al. |
| 2015/0360036 A1 | 12/2015 | Kane et al. |
| 2016/0038742 A1 | 2/2016 | Stahmann et al. |
| 2016/0059007 A1 | 3/2016 | Koop |
| 2016/0059022 A1 | 3/2016 | Stahmann et al. |
| 2016/0059024 A1 | 3/2016 | Stahmann et al. |
| 2016/0059025 A1 | 3/2016 | Stahmann et al. |
| 2016/0089539 A1 | 3/2016 | Gilkerson et al. |
| 2016/0228712 A1 | 8/2016 | Koop |
| 2016/0256692 A1 | 9/2016 | Baru |
| 2017/0021159 A1 | 1/2017 | Reddy et al. |
| 2017/0112399 A1 | 4/2017 | Brisben et al. |
| 2017/0113040 A1 | 4/2017 | Brisben et al. |
| 2017/0113050 A1 | 4/2017 | Brisben et al. |
| 2017/0113053 A1 | 4/2017 | Brisben et al. |
| 2018/0036527 A1 | 2/2018 | Reddy et al. |
| 2018/0036547 A1* | 2/2018 | Reddy .................. A61N 1/056 |
| 2018/0133462 A1 | 5/2018 | Reddy |
| 2018/0133463 A1 | 5/2018 | Reddy |
| 2018/0133494 A1 | 5/2018 | Reddy |
| 2018/0169384 A1 | 6/2018 | Reddy et al. |
| 2018/0169425 A1 | 6/2018 | Reddy et al. |
| 2018/0178018 A1 | 6/2018 | Reddy et al. |
| 2018/0178019 A1 | 6/2018 | Reddy et al. |
| 2018/0193060 A1 | 7/2018 | Reddy et al. |
| 2018/0214686 A1 | 8/2018 | De Kock et al. |
| 2018/0256890 A1 | 9/2018 | Fuhs et al. |
| 2018/0264270 A1 | 9/2018 | Koop et al. |
| 2018/0296824 A1 | 10/2018 | De Krock et al. |
| 2018/0325480 A1 | 11/2018 | Liu et al. |
| 2018/0344200 A1 | 11/2018 | Thakur et al. |
| 2018/0344252 A1 | 11/2018 | An et al. |

OTHER PUBLICATIONS

Schuder et al., "Experimental Ventricular Defibrillation with an Automatic and Completely Implanted System," Trans. Amer. Soc. Artif. Int. Organs, XVI: 207-212, 1970.

Schuder et al., "The Role of an Engineering Oriented Medical Research Group in Developing Improved Methods and Devices for Achieving Ventricular Defibrillation: The University of Missouri Experience," PACE, 16: 95-124, Jan. 1993.

Ghosh et al., "A Rare Malposition of the Thoracic Venous Catheter Introduced via the Left Internal Jugular Vein," Indian J. Crit. Care Med., 12(4): 201-203, Oct.-Dec. 2008.

Loukas et al., "The Clinical Anatomy of the Internal Thoracic Veins," Folia Morphol, 66(1): 25-32, 2007.

Advisory Action Before the Filing of an Appeal Brief for Application No. 15667167, dated Mar. 21, 2019.

Final Office Action for Application No. 15667167, dated Jan. 10, 2019.

Non-Final Office Action for Application No. 15667167, dated Jun. 26, 2018.

Non-Final Office Action for Application No. 15667167, dated Aug. 7, 2019.

Final Office Action for Application No. 15667221, dated Apr. 11, 2019.

Non-Final Office Action for Application No. 15667221, dated Oct. 1, 2018.

Notice of Allowance and Fees Due for Application No. 15667221, dated Jul. 11, 2019.

Amendment for Application No. 15667167, dated Sep. 17, 2018.
Amendment for Application No. 15667167, dated Oct. 9, 2019.
Amendment After Final Office Action for Application No. 15667167, dated Mar. 11, 2019.
Request for Continued Examination (RCE) for Application No. 15667167, dated Apr. 10, 2019.
Amendment for Application No. 15667221, dated Dec. 21, 2018.
Amendment After Final Office Action for Application No. 15667221, dated May 22, 2019.

* cited by examiner

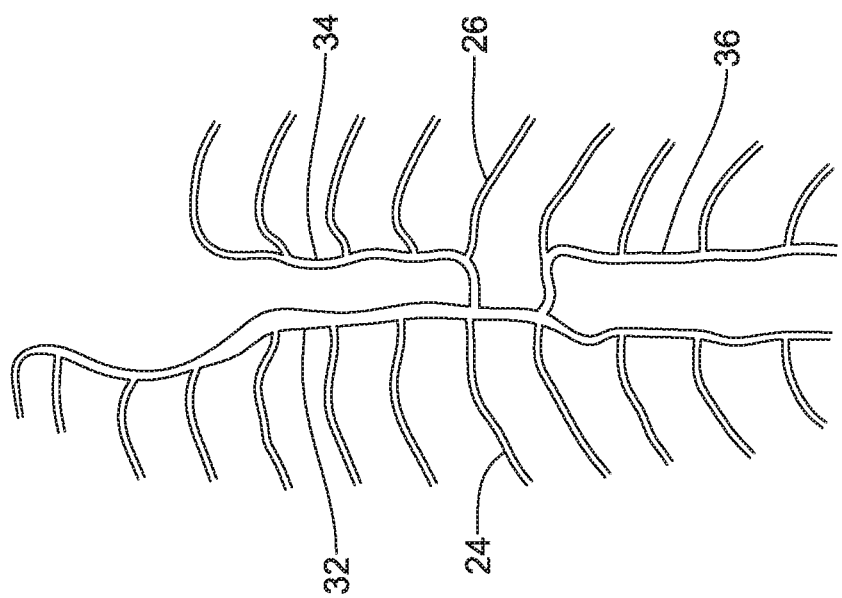

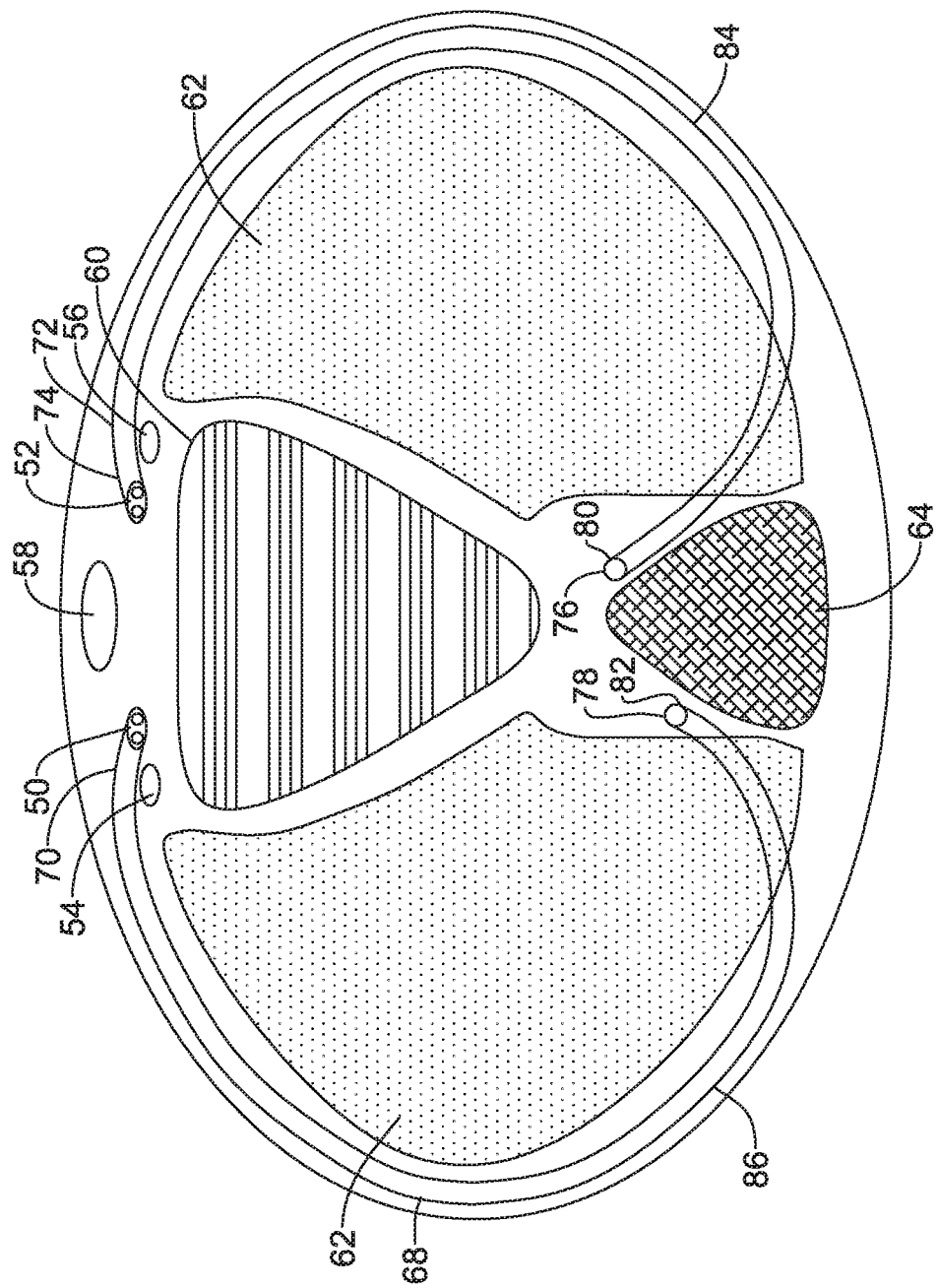

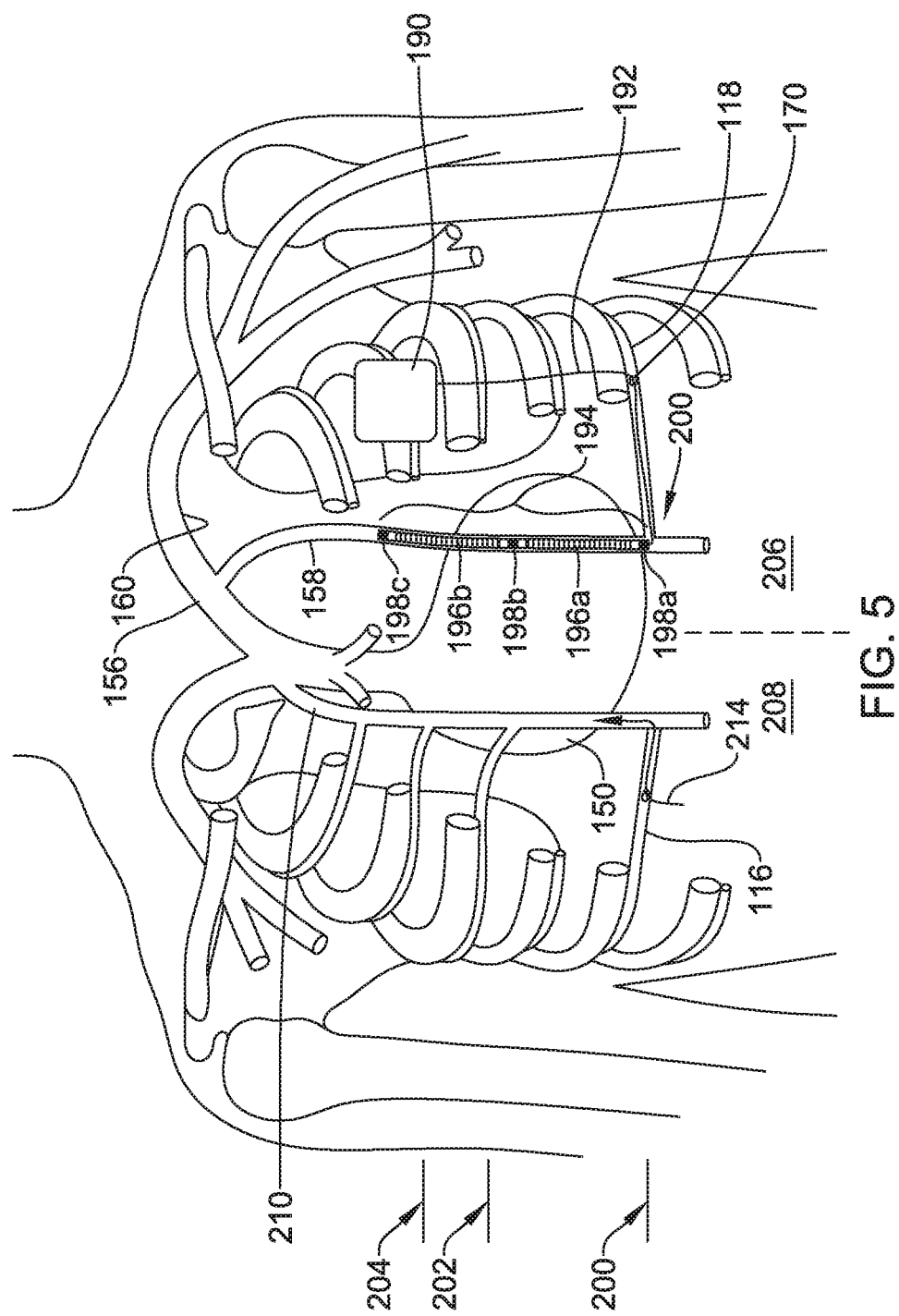

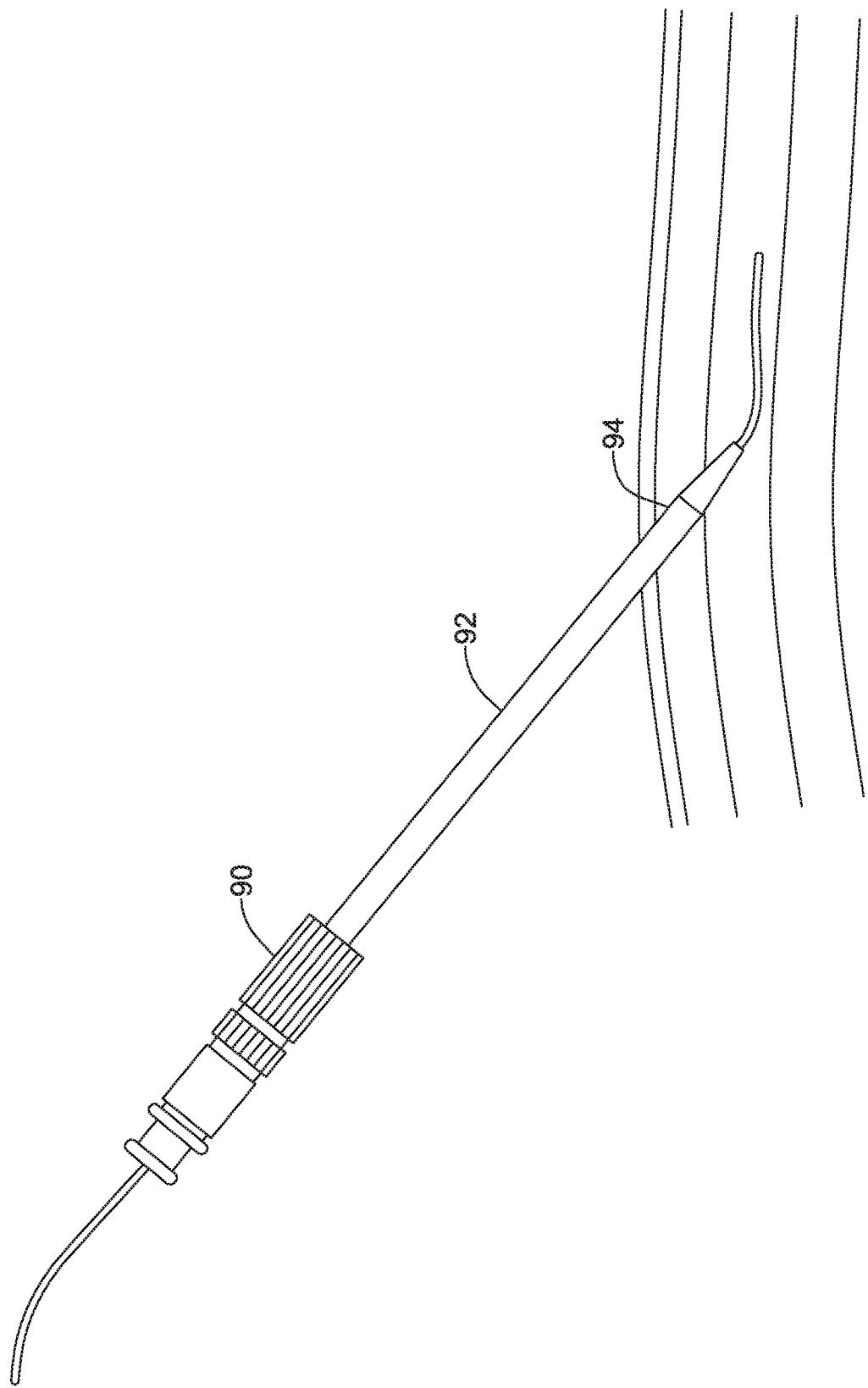

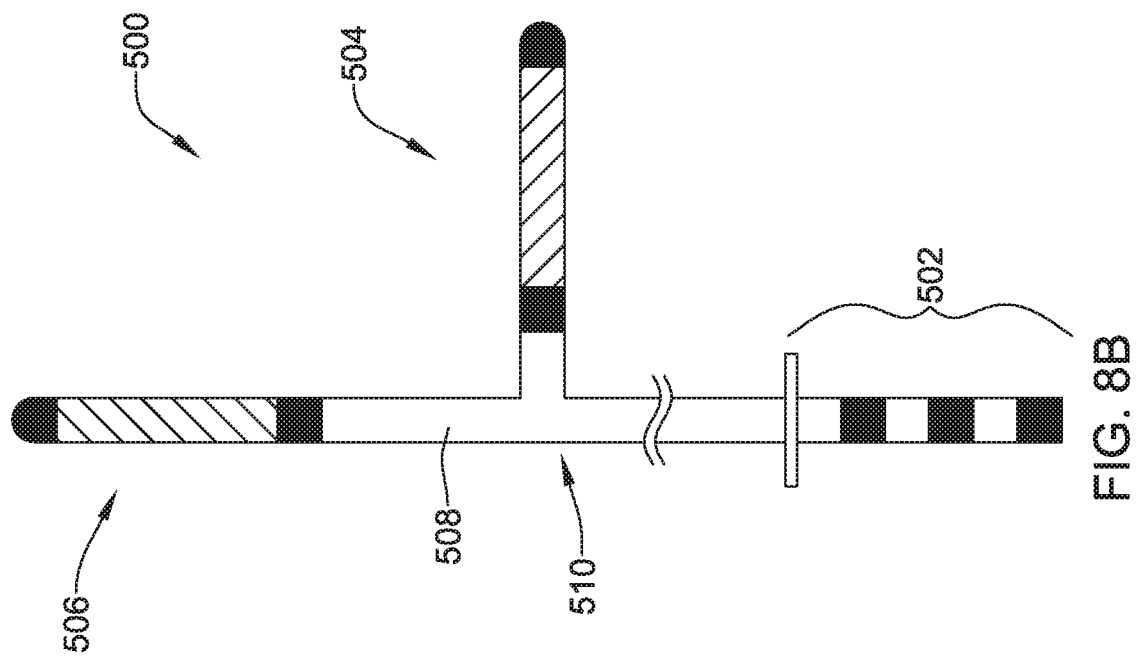

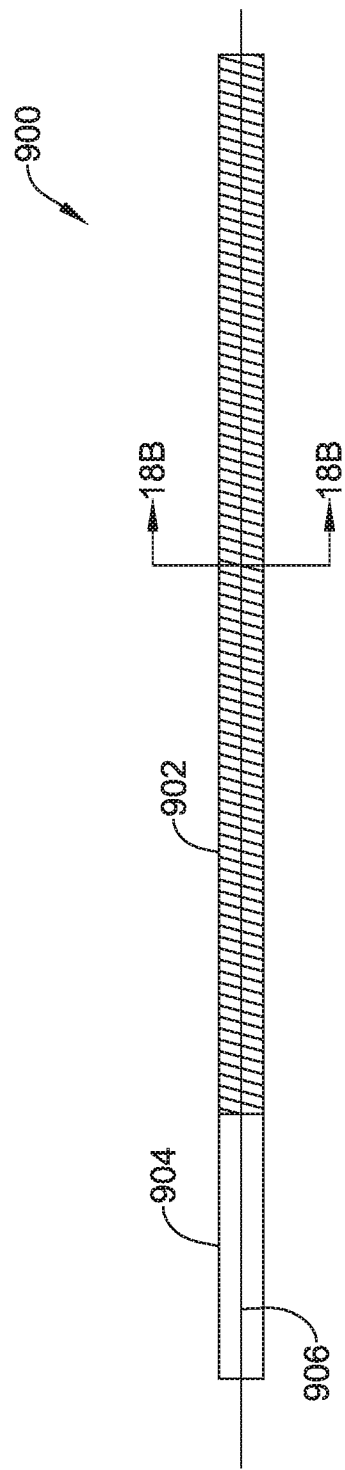
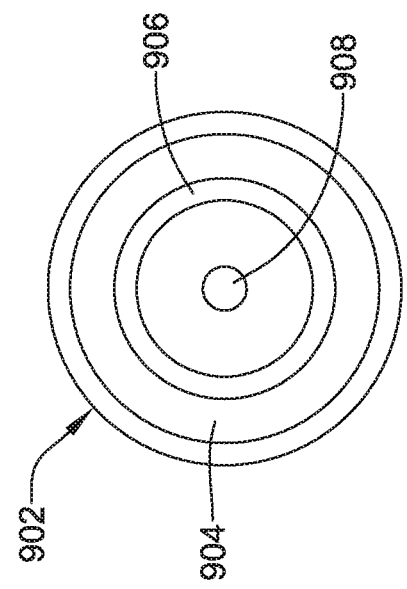

IMPLANTATION OF AN ACTIVE MEDICAL DEVICE USING THE INTERCOSTAL VEIN

CROSS REFERENCE TO RELATED APPLICATIONS

The present application claim the benefit of and priority to U.S. Provisional Patent Application Ser. No. 62/437,063, filed Dec. 21, 2016, titled IMPLANTATION OF AN ACTIVE MEDICAL DEVICE USING THE INTERCOSTAL VEIN, the disclosure of which is incorporated herein by reference.

BACKGROUND

The implantable defibrillator has been demonstrated to extend patient lives by treatment of potentially deadly arrhythmias. Over time, various efforts have been made to address complications associated with implantation of such devices. For example, early devices generally used epicardial patch electrodes implanted via thoracotomy, with attendant surgical risks and significant risks of failure of the epicardial patch electrodes and associated leads. The use of transvenous leads represented a major advance, avoiding the thoracotomy and improving reliability. However, lead failure remained a significant issue, as the lead attachment in the heart caused the lead to flex with each heartbeat. The advent of subcutaneous defibrillators allows avoidance of these lead failure issues, with leads implanted beneath the skin and over the ribcage of the patient and not subjected to the repeated flexing.

However, subcutaneous defibrillators require higher energy for defibrillation, causing the pulse generators for such systems to be larger than their transvenous predecessors, and both bradycardia pacing and anti-tachycardia pacing are of limited utility as such pacing subcutaneously can be very uncomfortable for the patient. This has led to interest in further alternative locations for implantable defibrillators, and other medical devices such as the implantable pacemaker.

Overview

The present inventors have recognized, among other things, that the internal thoracic vasculature including, in particular, the internal thoracic vein (ITV), sometimes also referred to as the internal mammary vein, presents an opportunity for an additional alternative implant location. Access to the ITV may be performed using the intercostal vein. A lead for an implantable cardiac device may then be implanted into one or both ITVs.

A first non-limiting example takes the form of a method of implanting a lead for use in a cardiac stimulus system in a patient, the lead having at least one electrode thereon; the method comprising inserting the lead in an internal thoracic vein (ITV) through an intercostal vein to a desired location relative to the heart of the patient.

Additionally or alternatively a second non-limiting example takes the form of a method as in the first non-limiting example further comprising establishing access to the intercostal vein of the patient and inserting an introducer sheath into the intercostal vein, and advancing at least the lead through the introducer sheath, into the intercostal vein, and then through an ostium of the ITV.

Additionally or alternatively a third non-limiting example takes the form of a method as in the second non-limiting example further comprising advancing a guidewire to and into the ostium of the ITV from the intercostal vein.

Additionally or alternatively a fourth non-limiting example takes the form of a method as in the second or third non-limiting examples further comprising advancing a guide catheter to and into the ostium of the ITV from the intercostal vein.

Additionally or alternatively a fifth non-limiting example takes the form of a method as in the second to fourth non-limiting examples further comprising advancing a needle into the intercostal vein.

Additionally or alternatively a sixth non-limiting example takes the form of a method as in the first non-limiting example further comprising establishing access to the intercostal vein at a costal groove on an inferior portion of a rib and introducing the lead through the intercostal vein and advancing the lead into the ITV.

Additionally or alternatively a seventh non-limiting example takes the form of a method as in the sixth non-limiting example, wherein the step of establishing access to the intercostal vein comprises inserting a needle into the intercostal vein; and advancing a sheath into the intercostal vein; and wherein the step of introducing the lead through the intercostal vein comprises advancing a distal end of the lead through the sheath and into the ITV.

Additionally or alternatively an eighth non-limiting example takes the form of a method as in the seventh non-limiting example, wherein the step of advancing the distal end of the lead through the sheath and into the ITV comprises advancing the distal end of the lead in a superior direction into the ITV.

Additionally or alternatively a ninth non-limiting example takes the form of a method as in the sixth to eighth non-limiting examples, wherein the step of establishing access to the intercostal vein includes using ultrasound guidance.

Additionally or alternatively a tenth non-limiting example takes the form of a method as in the sixth to eighth non-limiting examples, wherein the step of establishing access to the intercostal vein includes using a cut down procedure to expose the intercostal vein.

Additionally or alternatively an eleventh non-limiting example takes the form of a method as in the sixth to tenth non-limiting examples, wherein the intercostal vein is a left anterior intercostal vein.

Additionally or alternatively a twelfth non-limiting example takes the form of a method as in the sixth to tenth non-limiting examples, wherein the intercostal vein is a right anterior intercostal vein.

Additionally or alternatively a thirteenth non-limiting example takes the form of a method as in the first to eleventh non-limiting examples further comprising accessing the intercostal vein at a first location, creating a subcutaneous tunnel between the first location and a second location, placing the first lead to pass through the subcutaneous tunnel, connecting the first lead to an implantable canister for a system, and implanting the canister at the second location.

Additionally or alternatively a fourteenth non-limiting example takes the form of a method as in any of the preceding non-limiting examples, wherein the step of inserting the lead includes placing a stylet in the lead to hold the lead in a first configuration and, upon inserting the lead at the desired location, removing the stylet to release the lead into an expanded configuration relative to the first configuration.

Additionally or alternatively a fifteenth non-limiting example takes the form of a method as in the fourteenth non-limiting example wherein the first configuration is generally straight, and the second configuration is in the form of a spiral.

Additionally or alternatively a sixteenth non-limiting example takes the form of a method as in the first non-limiting example, wherein the lead further includes a second electrode thereon and the method further comprises placing the second electrode in the intercostal vein.

Additionally or alternatively a seventeenth non-limiting example takes the form of a method as in the first non-limiting examples, wherein the lead is inserted in the ITV through an anterior portion of the intercostal vein and the method further comprises inserting a second lead in a posterior portion of the intercostal vein to a second desired location.

Additionally or alternatively an eighteenth non-limiting example takes the form of a method as in the first non-limiting example, wherein the lead is inserted in the ITV through an anterior portion of the intercostal vein and the method further comprises inserting a second lead in an azygos vein through a posterior portion of the intercostal vein to a second desired location.

Additionally or alternatively a nineteenth non-limiting example takes the form of a method as in the first non-limiting example further comprising: making an incision for implantation of a canister to couple to the lead; accessing the intercostal vein through the incision; dissecting a pocket to receive the canister; connecting the canister to the lead; and implanting the canister in the pocket.

Additionally or alternatively a twentieth non-limiting example takes the form of a method as in the nineteenth non-limiting example further comprising inserting a second lead in the intercostal vein using access through the incision and advancing the second lead posterior of the pocket, wherein the pocket is approximately at the left axilla.

A twenty-first non-limiting example takes the form of a method of treating a patient comprising delivering therapy between an electrode on a first lead placed in an internal thoracic vein (ITV), the first lead having at least a portion passing through a portion of an intercostal vein, and a second electrode placed in the patient.

Additionally or alternatively a twenty-second non-limiting example takes the form of a method as in the twenty-first non-limiting example, wherein the first lead includes a high voltage coil.

Additionally or alternatively a twenty-third non-limiting example takes the form of a method as in the twenty-first non-limiting example, wherein the first lead includes at least one pacing electrode.

Additionally or alternatively a twenty-fourth non-limiting example takes the form of a method as in the twenty-first to the twenty-third non-limiting examples, wherein the second electrode is on or forms part of an implantable pulse generator canister housing operational circuitry for the system, the canister configured for use as at least one of a pacing electrode or a defibrillation electrode.

Additionally or alternatively a twenty-fifth non-limiting example takes the form of a method as in the twenty-fourth non-limiting example, wherein the implantable pulse generator is located in the patient's left axilla, and the first lead comprises an electrode in the left ITV.

Additionally or alternatively a twenty-sixth non-limiting example takes the form of a method as in the twenty-first to twenty-fifth non-limiting examples, wherein the therapy is a defibrillation therapy.

Additionally or alternatively a twenty-seventh non-limiting example takes the form of a method as in the twenty-first to twenty-fifth non-limiting examples, wherein the therapy is a bradycardia pacing therapy.

Additionally or alternatively a twenty-eighth non-limiting example takes the form of a method as in the twenty-first to twenty-fifth non-limiting examples, wherein the therapy is an anti-tachycardia pacing therapy.

Additionally or alternatively a twenty-ninth non-limiting example takes the form of a method as in the twenty-first to twenty-fifth non-limiting examples, wherein the therapy is a cardiac resynchronization therapy.

Additionally or alternatively a thirtieth non-limiting example takes the form of a method as in the twenty-first to twenty-fifth non-limiting examples, wherein the therapy is a right atrial pacing therapy.

Additionally or alternatively a thirty-first non-limiting example takes the form of a method as in the twenty-first non-limiting example wherein the second electrode is disposed on a second lead implanted in the patient.

Additionally or alternatively a thirty-second non-limiting example takes the form of a method as in the thirty-first non-limiting example wherein the first lead has a portion placed in a first ITV of the patient and the second lead has a portion placed in a second ITV of the patient.

Additionally or alternatively a thirty-third non-limiting example takes the form of a method as in the thirty-first non-limiting example wherein the first lead has a portion placed in a first ITV of the patient and the second lead has a portion placed within the heart of the patient.

Additionally or alternatively a thirty-fourth non-limiting example takes the form of a method as in the thirty-first non-limiting example wherein the first lead has a portion placed in a first ITV of the patient and the second lead has a portion placed on the posterior of the patient's chest.

Additionally or alternatively a thirty-fifth non-limiting example takes the form of a method as in the thirty-first non-limiting example, wherein the first lead has a portion placed in a first ITV of the patient and the second lead has at least a portion passing through a posterior portion of an intercostal vein such that the second electrode is in the posterior portion of the intercostal vein.

Additionally or alternatively a thirty-sixth non-limiting example takes the form of a method as in the thirty-first non-limiting example, wherein the first lead has a portion placed in a first ITV of the patient and the second lead has at least a portion passing through a posterior portion of an intercostal vein and extending into at least one of the azygos vein, the hemiazygos vein, or the accessory hemiazygos vein, such that the second electrode resides in the at least one of the azygos vein, the hemiazygos vein, or the accessory hemiazygos vein.

Additionally or alternatively a thirty-seventh non-limiting example takes the form of a method as in the twenty-first non-limiting example wherein the second electrode is disposed on the portion of the first lead that is within the intercostal vein.

Additionally or alternatively, another non-limiting example may take the form of an implantable cardiac stimulus device comprising a first lead, a second lead, and an implantable canister for coupling to the first and second leads, the implantable canister housing operational circuitry configured to deliver output therapy in the form of at least one of bradycardia pacing, anti-tachycardia pacing, cardiac resynchronization therapy, or defibrillation, according to a method as in any of the twenty-first to thirty-seventh non-limiting examples.

Additionally or alternatively, another non-limiting example may take the form of an implantable cardiac stimulus device comprising a lead and an implantable canister for coupling to the lead, the implantable canister housing operational circuitry configured to deliver output therapy in the form of at least one of bradycardia pacing, anti-tachycardia pacing, cardiac resynchronization therapy, or defibrillation, according to a method as in any of the twenty-first to thirty-seventh non-limiting examples.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 1B illustrates the posterior thoracic anatomy including placement of the azygos veins;

FIG. 2 shows the torso in a section view to highlight the location of the ITVs and other structures;

FIGS. 4-5 show access to and implantation of a lead in the left ITV from the left intercostal vein;

FIG. 6A-F shows access to the intercostal vein using the Seldinger technique;

FIG. 8B shows an illustrative lead that may be used in the implantation configuration of FIG. 8A;

FIGS. 18A-18D show an illustrative ITV shock coil lead structure.

DETAILED DESCRIPTION

Figure 1A:
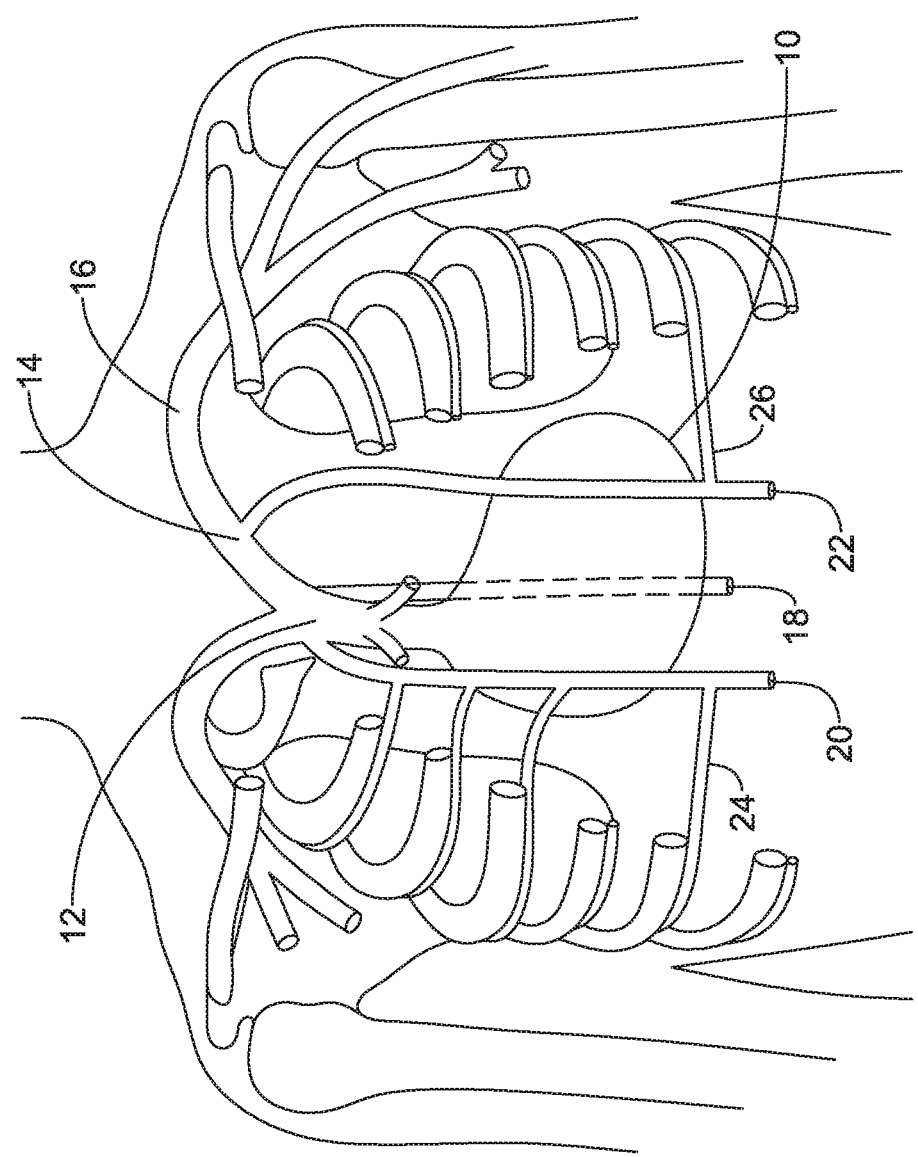
FIG. 1A illustrates the thoracic anatomy including placement of the internal thoracic veins (ITVs)

The S-ICD System from Boston Scientific provides benefits to the patient including the preservation of transvenous anatomy and avoidance of intracardiac leads, which may fracture and/or may serve as conduits for infection to reach the heart, and can occlude blood vessels going into the heart, making later placement of leads or other devices in the heart more difficult. Some examples and discussion of subcutaneous lead implantation may be found in U.S. Pat. No. 8,157,813, titled APPARATUS AND METHOD FOR SUBCUTANEOUS ELECTRODE INSERTION, and US PG Publication No. 20120029335, titled SUBCUTANEOUS LEADS AND METHODS OF IMPLANT AND EXPLANT, the disclosures of which are incorporated herein by reference. Additional subcutaneous placements are discussed in U.S. Pat. No. 6,721,597, titled SUBCUTANEOUS ONLY IMPLANTABLE CARDIOVERTER DEFIBRILLATOR AND OPTIONAL PACER, and the above mentioned U.S. Pat. No. 7,149,575, the disclosures of which are incorporated herein by reference.

While many patients can be well treated with the S-ICD System, there continue to be limitations. Increased energy requirements of the S-ICD System, perceived difficulty with providing chronic bradycardia pacing, and unavailability of anti-tachycardia pacing to terminate select fast tachycardias, have created interest in alternative defibrillator and/or pacemaker placement techniques. One proposal has included a substernal placement, with a lead extending beneath the sternum from a position inferior to the lower rib margin, such as in US PG Pat. Pub. No. 20170021159, titled SUBSTERNAL PLACEMENT OF A PACING OR DEFIBRILLATING ELECTRODE, the disclosure of which is incorporated herein by reference. Proposals for a substernal device have been referred to as extravascular, insofar as the lead does not enter or reside in the vasculature. Such devices are distinct from early generation epicardial devices in that the lead and electrode would not touch the heart or enter or be secured to the pericardium.

The present inventors have identified still a further alternative. In human anatomy, the internal thoracic vein (ITV), which may also be referred to as the internal mammary vein, is a vessel that drains the chest wall and breasts. There are both left and right internal thoracic veins on either side of the sternum, beneath the ribs. The ITV arises from the superior epigastric vein, accompanies the internal thoracic artery along its course and terminates in the brachiocephalic vein. The inventors have recognized that the ITV may make a suitable location for placement of a cardiac stimulus lead. While much of the following disclosure focuses on the use of the ITV, many of these concepts could also be applied to the internal thoracic arteries, which may sometimes be referenced as the internal mammary arteries. Some additional details related to the use of the ITV for placement of cardiac leads may be found in U.S. patent application Ser. No. 15/667,167, titled IMPLANTATION OF AN ACTIVE MEDICAL DEVICE USING THE INTERNAL THORACIC VASCULATURE, the disclosure of which is incorporated herein by reference.

FIG. 1A illustrates the thoracic anatomy including location of the internal thoracic veins (ITVs) 20, 22. A right intercostal vein 24 may couple to the right ITV 20 and a left intercostal vein 26 may couple to the left ITV 22. The right and left intercostal veins 24, 26 may each run along a costal groove on an inferior portion of a rib. Additionally, an artery (not shown) and a nerve (not shown) may be located inferior (in that order) to the intercostal veins 24, 26 and also run along the costal groove. An outline of the heart is shown at 10, with the superior vena cava (SVC) shown at 12. The brachiocephalic veins 14 couple to the SVC 12 and extend past various cephalic branches to the subclavian vein 16. The azygos vein is also shown at 18.

Certain literature in the field of implantable pacemakers or defibrillators has noted the possibility of the using the azygos vein 18 to implant a lead and electrode to stimulate the vagus nerve (see, for example, U.S. Pat. No. 8,005,543, the disclosure of which is incorporated herein by reference), or as an adjunct to defibrillator function (see Cesario et al., "Azygos vein lead implantation: a novel adjunctive technique for implantable cardioverter defibrillator placement," J. Cardiovasc. Electrophysiol., 2004, 15:780-783). However, such proposals have not found widespread acceptance, and it does not appear that the ITVs 20, 22 have been proposed.

FIG. 1B illustrates the posterior anatomy including placement of the azygos vein, 32, accessory hemiazygos vein 34, and hemiazygos vein 36. The right intercostal vein 24 may run posteriorly along the costal groove on the inferior portion of the right rib and may couple to the azygos vein 32. The left intercostal vein 26 may run posteriorly along the costal groove on the inferior portion of the left rib and may couple to the accessory hemiazygos vein 34. In various embodiments, a left and/or right intercostal vein, at any suitable level of the torso, may be selected and used for implantation of an electrode and lead for use in delivering cardiac therapy. The intercostal veins 24, 26 may be a final implant location or may provide an avenue for implantation in another part of the anatomy such as in the ITV, the mediastinum, and/or the azygos vein 32, hemiazygos vein 36, or accessory hemiazygos vein 34.

FIG. 2 shows the torso in a section view to highlight the location of various vascular structures. More particularly, in the example, the left and right ITV are shown at 50, 52, running parallel to and more central of the internal thoracic arteries 54, 56, on either side of the sternum 58. The heart is shown at 60, with the lungs at 62 and spinal column at 64. The ITV 50, 52 lie beneath the ribs but outside and separate from the pleurae of lungs 62. The ribs are omitted in the drawing in order to show the intercostal veins. The left anterior intercostal vein 68 runs along the inferior portion of a rib and couples to the left ITV 50 at junction 70, forming an ostium at the point where the left anterior intercostal vein 68 flows into the left ITV 50. Additionally, the right intercostal vein 72 runs along the inferior portion of another rib and couples to the right ITV 52 at junction 74, forming an ostium at the point where the anterior intercostal vein 72 flows into the right ITV 52. As used herein, the "ITV" is the name applied for the vein while it runs beneath the chest, that is, superior to the lower margin of the ribs. Inferior of this location, the blood vessel is referred to (at least in this description) as the superior epigastric vein.

An azygos vein and a hemiazygos vein are shown at 76, 78, running parallel to and on either side, more or less, of the spinal column 64. The azygos vein 76 and the hemiazygos vein 78 also lie beneath the ribs but outside and separate from the pleurae of lungs 62. The left posterior intercostal vein 86 couples to the hemiazygos vein 78 at a junction 82, forming an ostium at the point where the intercostal vein 68 flows into the hemiazygos vein 78. Additionally, the right posterior intercostal vein 84 couples to the azygos vein 76 at a junction 80, forming an ostium at the point where the intercostal vein 72 flows into the azygos vein 76.

Figure 3B:
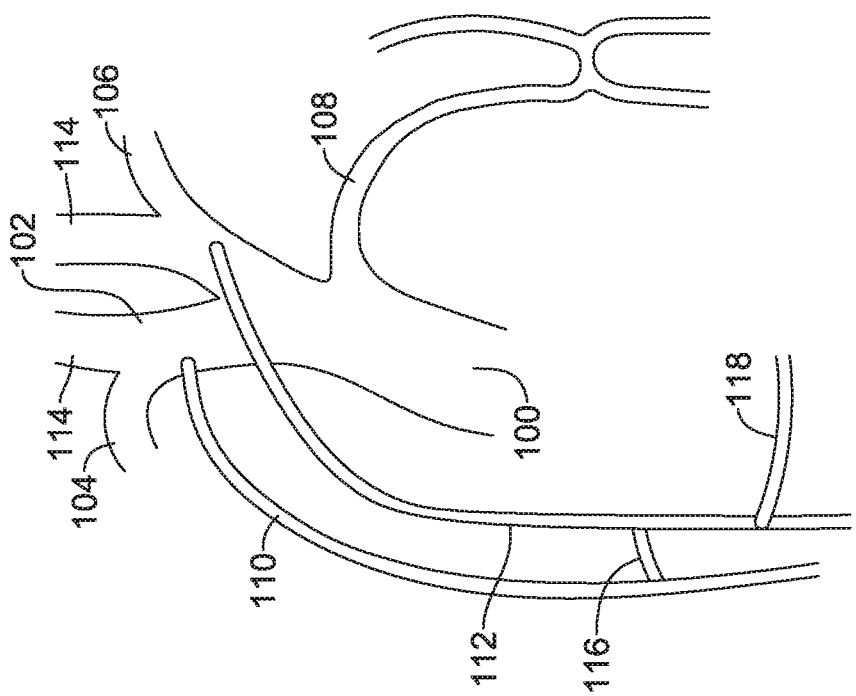
FIGS. 3A-3B show the ITVs and linked vasculature in isolation.
Figure 3A:
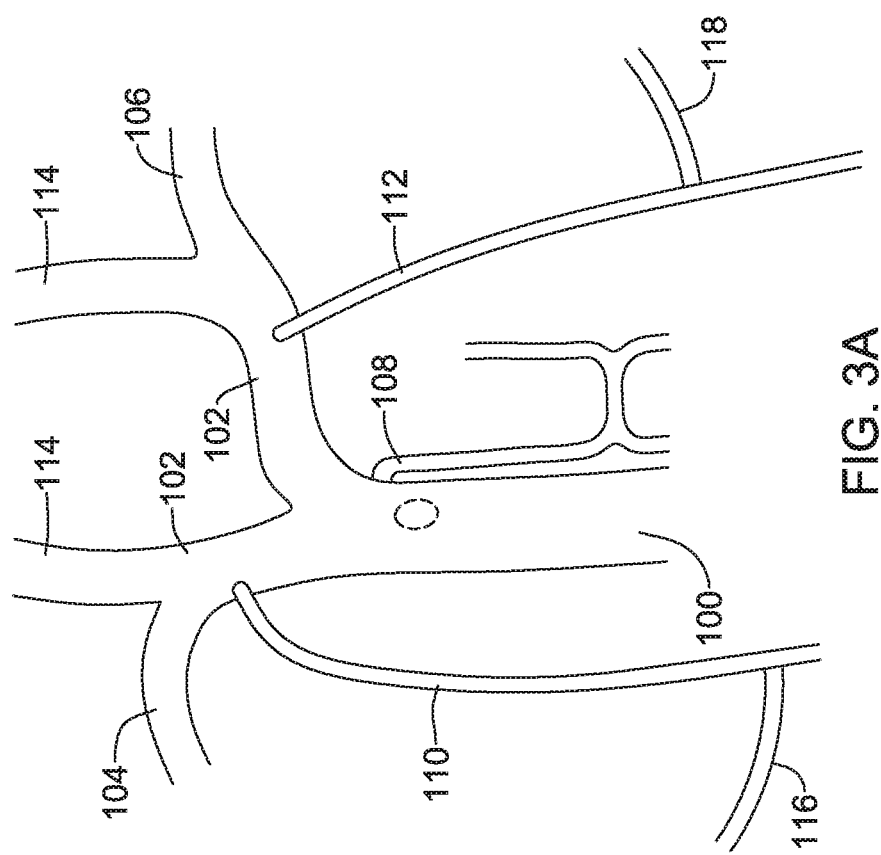

FIGS. 3A-3B show the ITV and linked vasculature in isolation. FIG. 3A is an anterior view of selected portions of the venous structure of the upper torso, and FIG. 3B is a lateral view of the same. The SVC is shown at 100, with the brachiocephalic veins 102 splitting at the upper end of the SVC. The right subclavian vein is at 104, and the left subclavian vein is at 106. The azygos vein is included in the illustration at 108, extending off the posterior of the SVC, and running inferiorly posterior of the heart as can be understood from the lateral view of FIG. 3B. The right and left ITV are shown at 110, 112. These each branch off at a location that is considered part of the brachiocephalic veins 102. Selected right and left intercostal veins are shown at 116, 118. There are left and right intercostal veins along the lower margin of each of the ribs. In several embodiments the intercostal veins of the $4^{th}$, $5^{th}$, or $6^{th}$ ribs are proposed for implantation of a lead with access through the intercostal vein to the ITV. In one example, the intercostal vein of the $6^{th}$ rib is accessed. In other examples, access may be more superior or inferior than these locations, as desired. These may branch off at a location of the right and left ITV's and continue to run along a coastal groove of an inferior portion of a the ribs. The internal jugular veins are also shown at 114.

Figure 4:
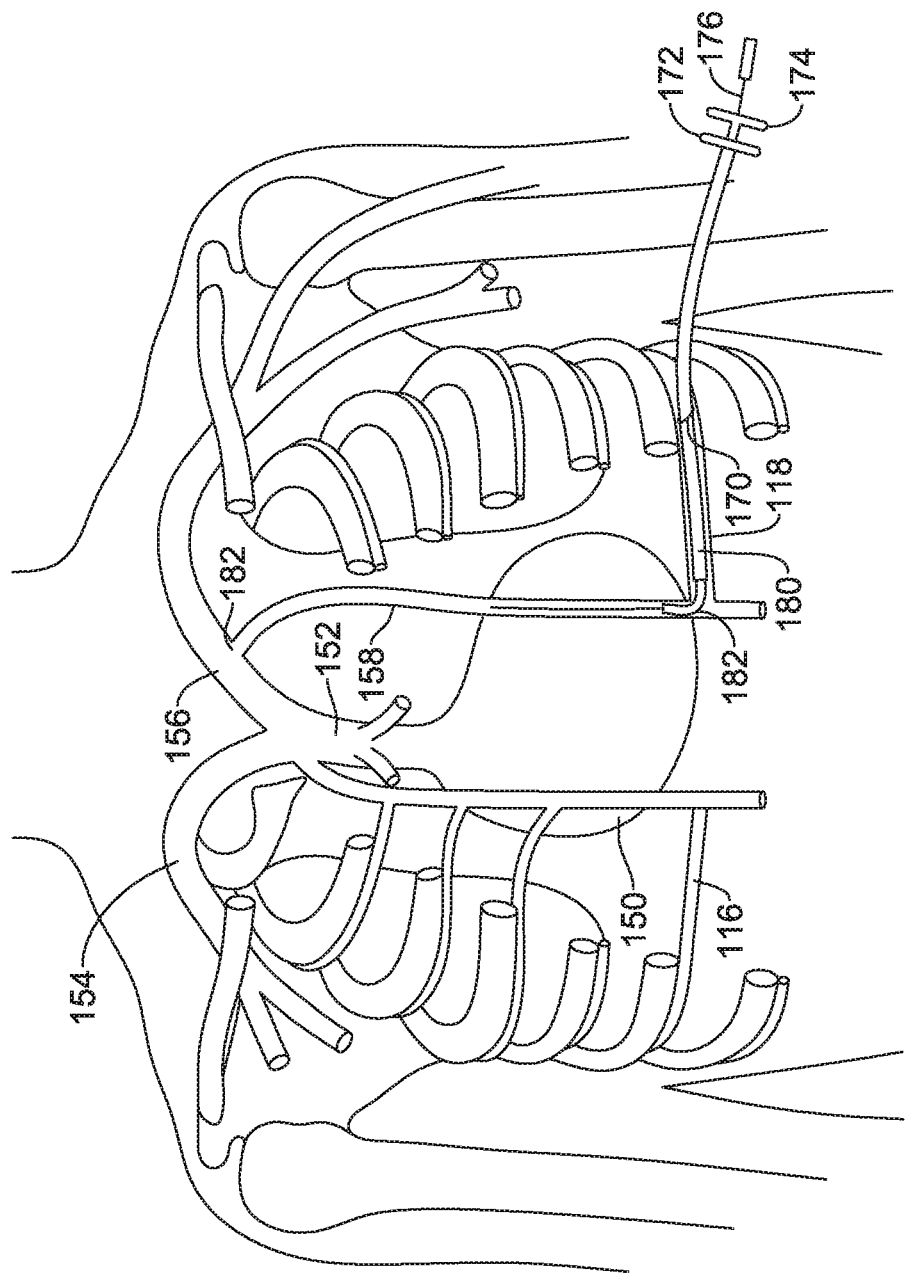

FIGS. 4-5 show access to and implantation of a lead in the ITV by way of an intercostal vein; in the example shown, the $6^{th}$ intercostal vein is used. Starting with FIG. 4, the heart is shown at 150 with the SVC at 152, the brachiocephalic vein right branch at 154 and left branch at 156, and a right intercostal vein at 116 and a left intercostal vein at 118. Access to the left intercostal vein 118 is shown at 170 using standard access techniques known in the art for implanting traditional transvenous pacemakers and defibrillators.

Figure 6A:
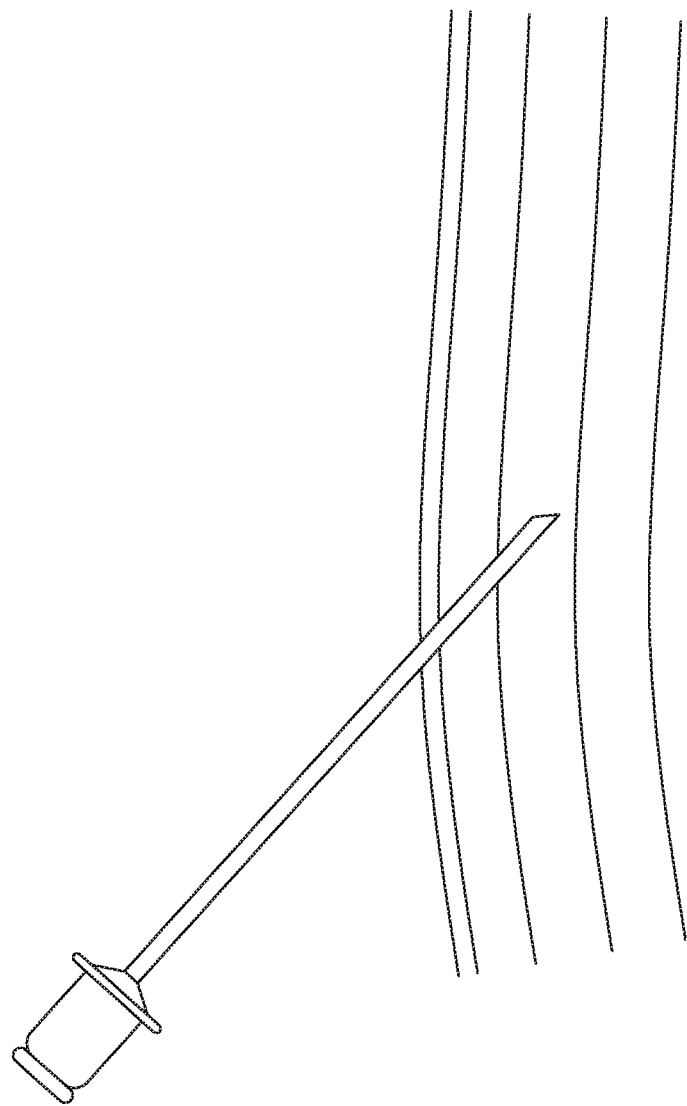
Figure 6B:
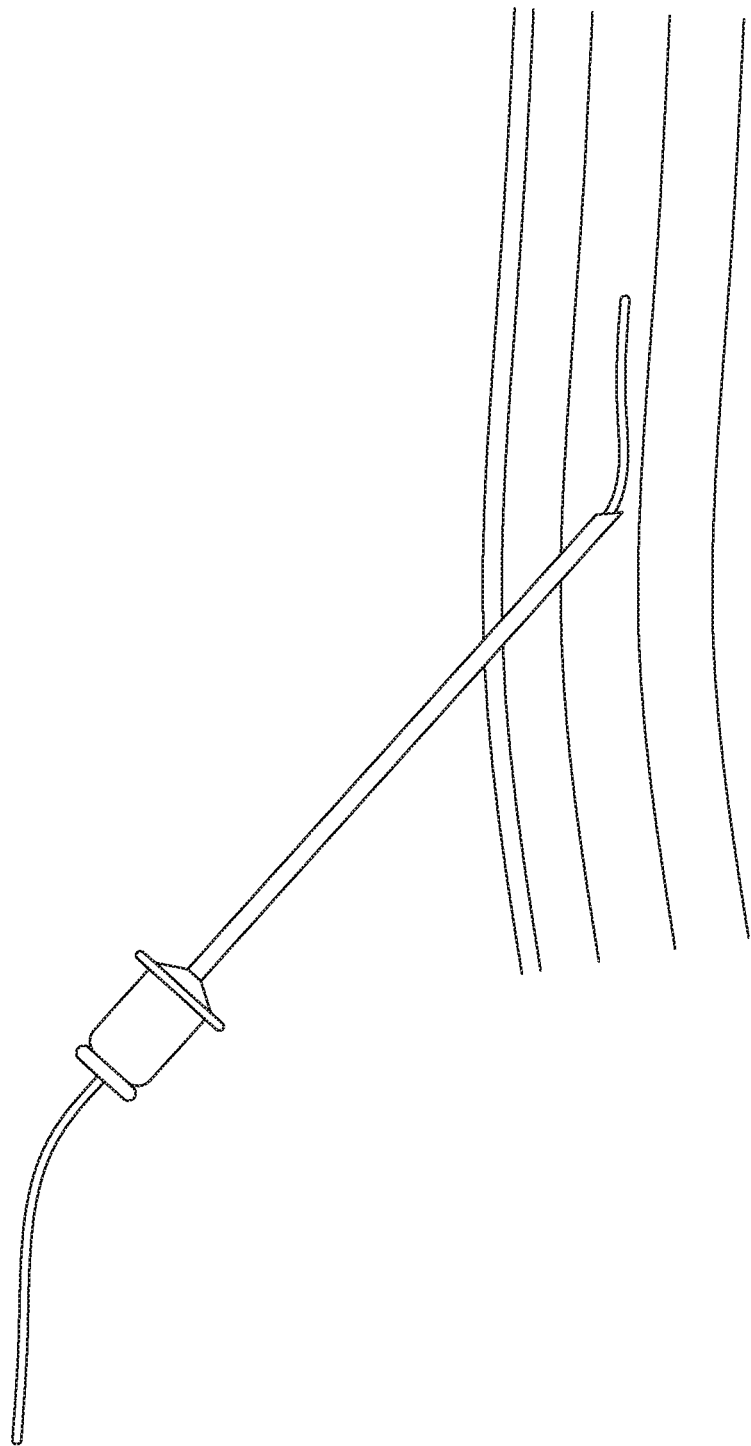
Figure 6C:
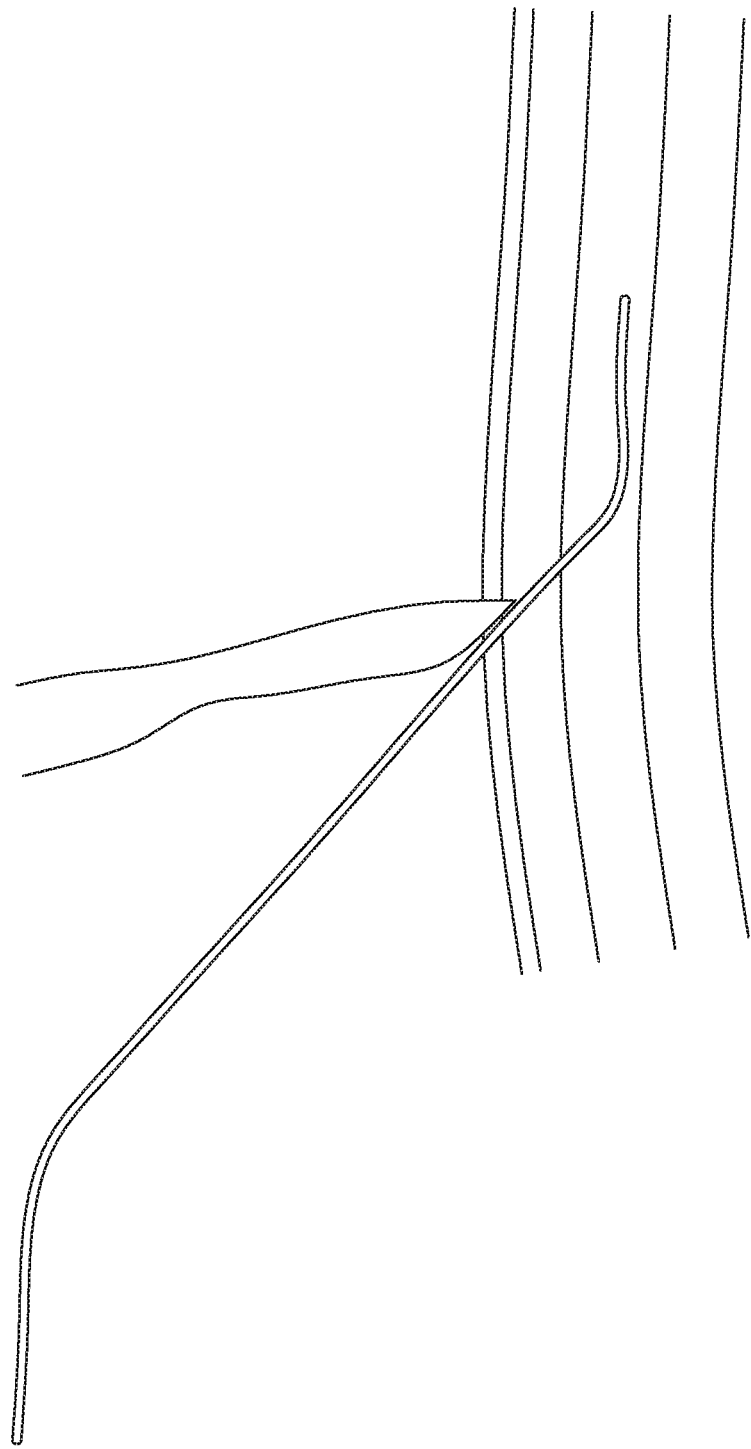
Figure 6D:
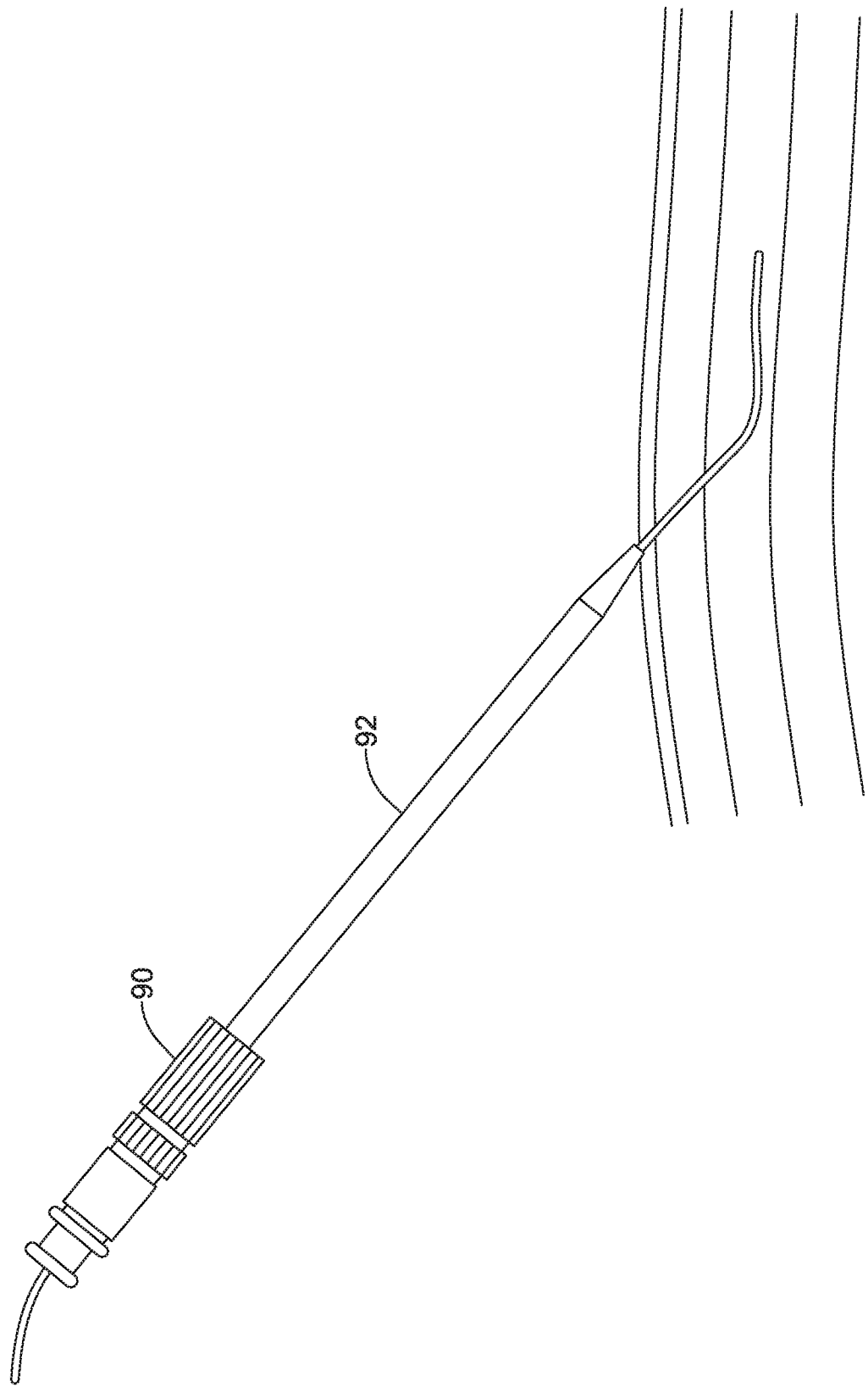
Figure 6F:
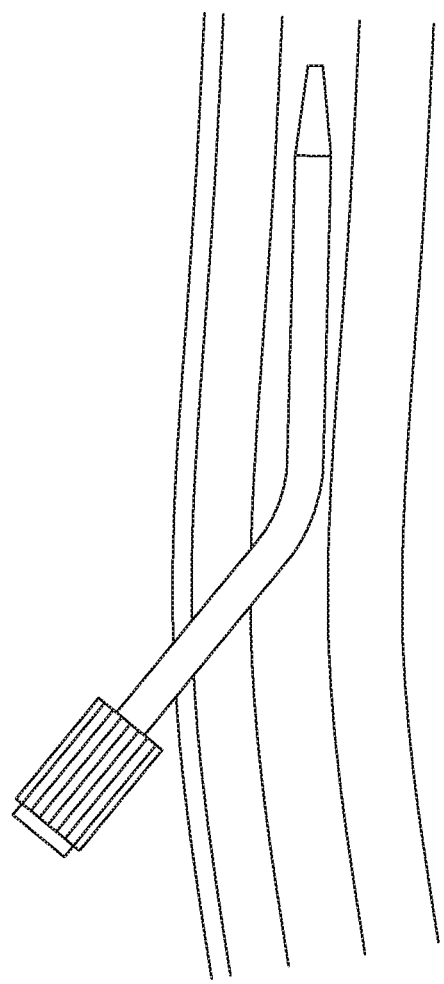

For example, as illustrated in FIGS. 6A-6F, the Seldinger technique may be used to gain entry to the intercostal vein. As shown in FIG. 6A, a puncture may be created with a hollow needle or trocar, for example under ultrasound guidance, to access the intercostal vein though the external and internal intercostal muscles; the innermost intercostal muscles should not be disturbed, preferably. As shown in FIG. 6B, a guidewire may be introduced through the needle. As shown in FIG. 6C, the needle may then be removed, with pressure applied at the point of the puncture to prevent blood outflow. As shown in FIG. 6D, an introducer sheath 90, which may have a valve at its proximal end, may then be inserted over the guidewire. As shown in FIG. 6E, the sheath 90 can be used to introduce a guide catheter 92 or other devices. The catheter 92 may include an inner telescoping catheter and may be straight and have a flexible distal tip 94 or a curved tip to enable advancing through the intercostal vein 118, as shown in FIG. 6F. At the conclusion of the lead implantation procedure, a sealing device such as a suture sleeve can be placed to seal the puncture site to the implantable lead left therein. In various embodiments, it may be desirable to achieve percutaneous lateral access of the left intercostal vein 118 near the inferior portion of the rib. Other venipuncture or cut-down techniques may be used instead. Such access may be performed, for example and without limitation, anywhere from about 2 cm left or right lateral to the sternum, up to about 10 cm left or right lateral of the sternal margin, as desired. In an example, access may be at about 6 cm from the sternal margin.

In other embodiments, the access location 170 may be located near or along a midaxillary line (not shown) of a patient. In one example, a canister housing operational circuitry for a system may be implanted in the left axilla of a patient, and access to a left intercostal vein is obtained using a cut-down or by use of an ultrasound needle from within a pocket formed subcutaneously to receive the canister. Access may thus range from the anterior axillary line to the midaxillary line and to the posterior axillary line, as desired. From this position, an anterior-posterior vector for sensing, transthoracic impedance measurement, and/or therapy delivery may be obtained by advancing two leads through an intercostal vein—with one advanced toward the sternum and the other toward the spine. The lead advanced toward the sternum may reside in the intercostal vein, or it may be advanced into the ITV and, from there, it may further go into the mediastinum if desired. The lead advanced toward the spine may reside in the intercostal vein, or it may be advanced to another structure, which may include the accessory hemiazygos vein and/or hemiazygos vein; if desired, the lead may even be advanced to the azygos vein.

Referring again to FIG. 4, into the access at 170, an introducer sheath 172 is inserted and advanced to a location to place its distal tip 180 near the ostium where the selected intercostal vein opens into the left ITV 158. Contrast injection may be useful to visualize the ITV structures and the ostia of the ITVs. A guide catheter 174 and guidewire 176 are then introduced through the introducer sheath 172. In other examples, a shorter introducer sheath may be used, with the guide catheter 174 used to traverse the distance to the relevant ostium, or a longer introducer may be used with a steerable guidewire, omitting the guide catheter entirely.

The guidewire 176 may be the same as used in gaining initial access 170 (if one is used to gain access 170), or may be a different guidewire. In an example, the guidewire 176 is preloaded in the guide catheter and both are introduced at the same time until the guide catheter 174 is at a desired location relative to the ostium of the selected ITV. The guidewire 176, which may be deflectable or steerable, can then be used to enter the left ITV 158 through the ostium thereof, passing up, in a superior direction, into the left ITV 158. The guide catheter 174 can then traverse over the guidewire and through the ostium and into the left ITV 158.

A device passing into the ITV 158 from the left intercostal vein 118 will pass through the valves of the ITV in a superior direction, corresponding to their natural tendency. In some embodiments, the guidewire may preferably be stiff. In other embodiments, the guidewire may be preferably flexible. In some examples, at least two guidewires may be used, a first more flexible and steerable guidewire to obtain initial access via the ostium of the ITV, and a second, stiffer guidewire to allow passage in the ITV.

In some examples, the guide catheter 174 is introduced first and the guidewire 176 is introduced next. For example, a steerable or curved guide catheter 174 may traverse the introducer sheath 172 to its distal end 180 and then, using steering of the guide catheter, a precurved structure of the guide catheter, or an inner telescoping catheter of the guide catheter, would then turn as shown at 182 to enter the left ITV 158. The guidewire 176 may be introduced through the guide catheter 174. In another example, a guidewire 176 may be omitted.

Furthermore, in various embodiments, a second lead may be implanted in or near an accessory hemiazygos vein using access 170. In this case, the intercostal vein 118 approach may be used to advance through the posterior portion of the intercostal vein 118 to a location near the ostium where the selected intercostal vein opens into the accessory hemiazygos vein. Additionally, in some cases, if a lower or inferior intercostal vein is chosen, a similar intercostal vein approach may be used to implant a second lead in or near a hemiazygos vein. According to various embodiments, the implantation of a second lead in the accessory hemiazygos vein and/or hemiazygos vein, may provide a good anterior to posterior vector.

This intercostal vein 118 approach may preserve the upper thoracic vasculature in the event that the patient later needs a traditional transvenous, intracardiac system, or for use in other procedures. Such access may also reduce the potential for lead fracture such as that caused by subclavian crush. Once access to the intercostal vein 118 is achieved, the intercostal vein 118 can be traversed to place the lead at a desired level by entering the corresponding ITV 158.

In another example, a cut-down technique may be used to access the intercostal vein 118 by incision through the skin. Next, possibly after visual confirmation by ultrasound guidance, for example, the desired vessel is accessed, incision into the intercostal vein 118 can be made. In another example, anatomical landmarks such as the rib margin and/or infrasternal angle may be used to facilitate venipuncture into the intercostal vein 118.

In animal testing the present inventors have determined that access to the ITV can be achieved with little difficulty to facilitate lead placement by accessing the intercostal vein 118. However it is recognized that the human anatomy will be different from that of the tested animal (porcine model), and may further vary with the particular body characteristics of a given patient including, for example, any venous abnormality, scarring in the area (such as related to any prior sternotomy or the like) as well as the body habitus (overweight or underweight patients).

FIG. 5 shows implantation of an implantable cardiac stimulus system. The system includes an implantable pulse generator 190 which may be placed in the subclavicular location shown (or any other suitable position, as desired). A lead 192 passes into the venous access point 170 into the intercostal vein 118. The lead then enters the left ITV 158. For such an introduction, in one example, the guide catheter 174 (FIG. 4) can be used to direct the lead 192 through the ostium of the chosen ITV, with or without use of a guidewire 176 (FIG. 4).

In some examples, a flexible lead is used having a lumen therein to receive a guidewire or stylet to enhance pushability through the ITV 158. In another example, a flexible lead may be introduced with the support of the guide catheter 174 during advancement. In this latter example, the guide catheter 174 may receive the lead 192 through a guide catheter lumen that serves to retain a fixation apparatus or shape for the flexible lead, such as a 2-dimensional or 3-dimensional curvature (see FIGS. 9-10), tines (see FIG. 11), an expandable member (see FIG. 14), or hooks or a side-extending engagement structure (see FIG. 15).

In another alternative, the guide catheter 174 and guidewire 176 may be omitted by providing a lead with a flexible or steerable structure, and/or a lead configured for implantation using a steerable stylet. For example, a lead may be configured to be implanted using a steerable stylet in a lumen thereof. Once initial access is achieved, simply pushing the stylet should be sufficient to implant the lead to a desired level in the ITV. The stylet may have a secondary function of preventing an anchoring structure of the lead from assuming an anchoring shape or releasing an anchoring tine, hook, expandable member, stent or other device.

In the example, the lead 192 includes a multi-electrode distal structure as shown at 194. The structure includes a proximal coil 196A separate from a distal coil 196B. In another embodiment, the distal coil 196B may be located in the ITV 158 and the proximal coil 196A may be located in the intercostal vein 118, and therapy may be delivered therebetween if desired. In various embodiments, the proximal coil 196A and/or distal coil 196B may be high voltage coils. The coils 196A/B and canister 190 may also serve as therapy delivery or pacing electrodes. As such there may be multiple therapy vectors such as between coil 196A and coil 196B, between either of coils 196A and 196B and the canister 190, or between a combination of two of the three therapy electrodes 196A, 196B and canister 190, and the third such electrode, such as by linking coils 196A and 196B in common as the anode or cathode relative to the canister 190.

A plurality of ring electrodes may be provided as shown at 198A, 198B, and 198C. Electrode 198C may also or instead be a tip electrode. Electrodes 198A/B/C may serve as sensing electrodes. The coils 196A, 196B may also serve as sensing electrodes. A lead and electrode may be as shown in U.S. Provisional Patent Application No. 62/437,064, filed Dec. 21, 2016, and titled LEAD WITH INTEGRATED ELECTRODES, the disclosure of which is incorporated herein by reference. These various electrodes may be used for sensing cardiac signals in various combinations using, for example, methods and circuitry discussed in U.S. Pat. No. 7,783,340, titled SYSTEMS AND METHODS FOR SENSING VECTOR SELECTION IN AN IMPLANTABLE MEDICAL DEVICE USING A POLYNOMIAL APPROACH, and U.S. Pat. No. 8,483,843, SENSING VECTOR SELECTION IN A CARDIAC STIMULUS DEVICE WITH POSTURAL ASSESSMENT, and/or US PG Patent Application Pub. Nos. 20170112399, 20170113040, 20170113050, and 20170113053, the disclosures of which are incorporated herein by reference.

In addition, one or more of the ring or tip electrodes 198A, 198B, 198C may be used for therapy delivery. In an example, defibrillation therapy may use coils 196A, 196B coupled in common as the opposing pole to the canister 190, while pacing therapy may use coils 196A and 198B as opposing electrodes for post-shock pacing therapy, with a still different combination of electrodes used to provide ventricular pacing therapy for example by pacing between coil 196B and tip electrode 198C.

Line 202 is provided, illustratively, to separate the atria and ventricles. The lead 192 may be placed as shown such that the proximal coil 196A is about level with the ventricles, and distal coil 196B is about level with the atria, if desired. In some examples fewer or different electrodes may be provided on the lead 192 such as by excluding one or the other of the proximal coil 196A or distal coil 196B. Various designs are also shown herein.

Line 204 is provided to indicate the top of the heart, with the apex or bottom of the heart marked at 200. In some examples, one or more electrodes on the lead 192 are provided at or inferior to the apex 200, or at or superior to the top 204 of the heart. In the example shown, on the other hand, the electrodes are located generally between the apex 200 and top 204 of the heart.

The illustration shown in FIG. 5 places the lead on the left side 206 of the patient. In other examples, the right side 208 of the patient may instead or in addition be accessed, including the right ITV 210. Access to the right ITV 210 may be achieved as shown at arrow 214 by entering the right intercostal vein 116 in a mirror image procedure of that shown in FIG. 4. In some examples, each of the left and right ITV 158, 210 may receive a lead 192. The lead 192 may be split (as shown in FIG. 8B), a yoke may be provided near the canister 190 to join two leads together, or a header on the canister 190 may be configured to receive more than one lead 192, if desired, to provide leads in each of the left and right ITV 158, 210.

Figure 8A:
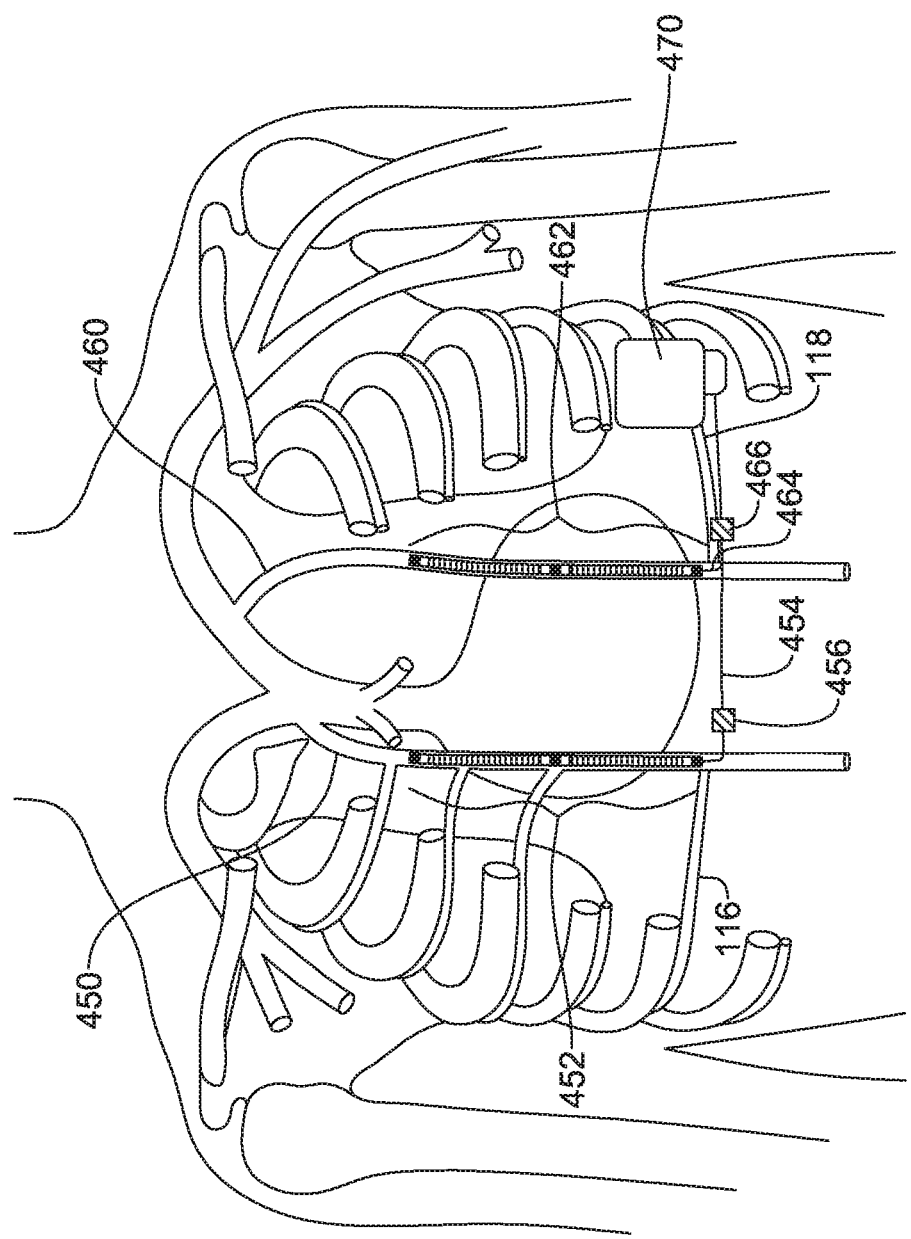
FIG. 8A shows implantation from the right and left intercostal veins into both ITVs.

If two leads are provided, use may be similar to that explained relative to FIG. 8A. For example, pacing between right and left side lead placements may be performed to target specific chambers or chamber combinations, or sensing may be performed using one pair of electrodes with therapy delivery using a different pair of electrodes to achieve resynchronization or other desirable effect. In some examples, one of the ITV may be accessed via an intercostal vein, while the other is accessed more directly using a parasternal implantation directly to the ITV. In other examples, each of the left and right ITV may be accessed, with both entries accomplished via respective intercostal veins. In other examples, one of the ITV may be accessed via an intercostal vein for lead placement accompanied by a traditional subcutaneous lead. In this embodiment, the traditional subcutaneous lead may provide defibrillation and the ITV lead may provide pacing and/or sensing therapy. In further embodiments, one of the ITV may be accessed via an intercostal vein for lead placement accompanied by implantation of a leadless cardiac pacemaker (LCP).

In some examples, rather than accessing the ITV from an anterior intercostal vein at a relatively lower part of the chest as shown in FIG. 5, the ITV may be accessed in a more superior position, such as near the $2^{nd}$ to $4^{th}$ ribs, or about level with the location of the canister 190 shown in FIG. 5. From this more superior entry to the ITV, the lead 192 may then be passed inferiorly to place shock, sensing and/or pacing electordes at a desired level relative to the patient's heart. In still other examples, an intermediate position may be selected and a lead or leads passed inferiorly and superiorly. In still further examples, first and second intercostal veins may be accessed to provide two entry points into the ITV, allowing a first lead implanted via a first intercostal vein to be advanced in a superior direction, and a second lead implanted via a second intercostal vein to be advanced in an inferior direction.

Figure 7:
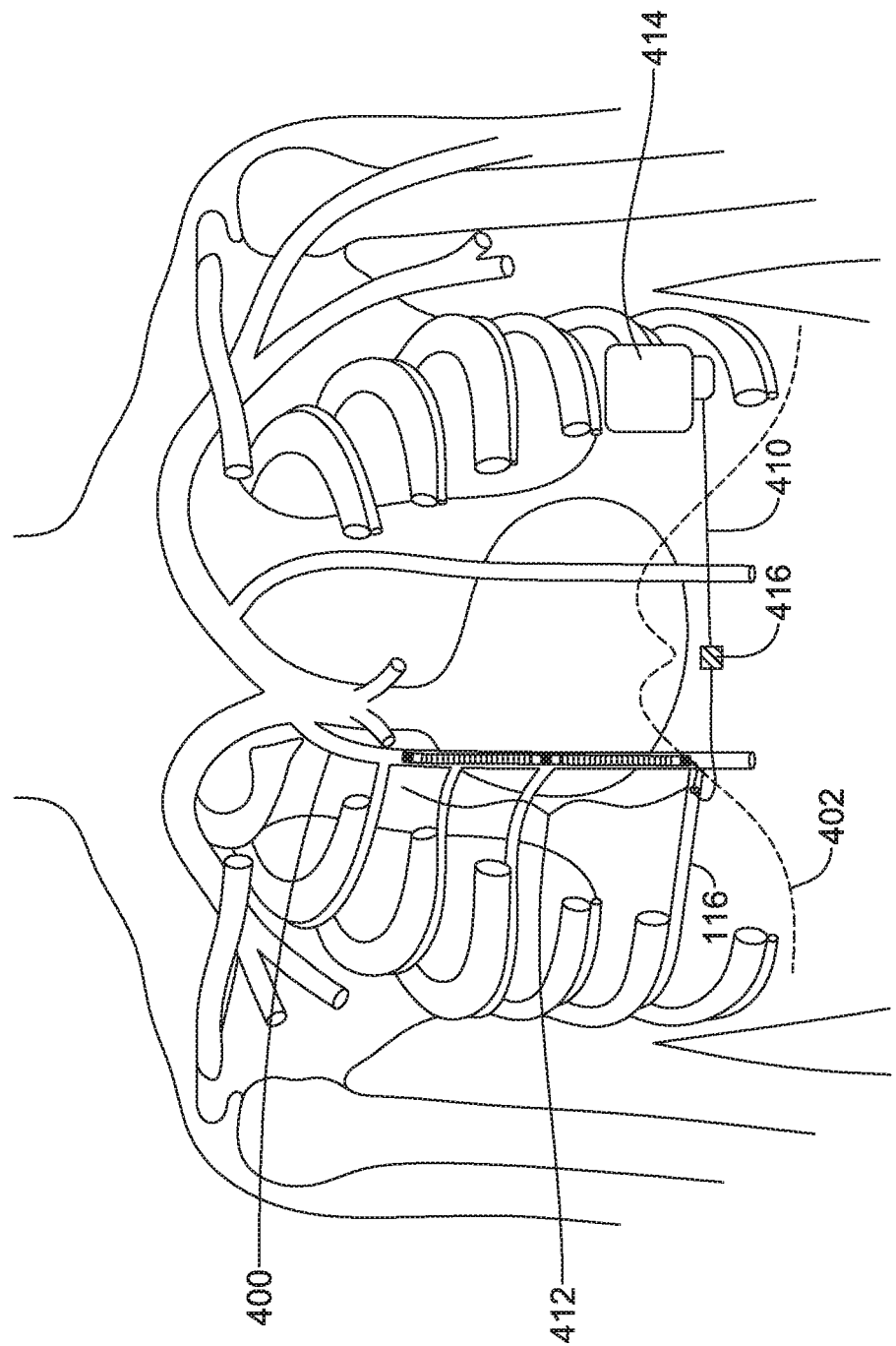
FIG. 7 shows implantation from the right intercostal vein to the right ITV.

FIG. 7 shows implantation from the right intercostal vein 116. In this example, the right ITV 400 has been accessed. An implantable device has been placed including a lead 410 having a distal electrode structure 412 and a canister 414, with the canister 414 placed at approximately the left axilla. The canister 414 may be placed as desired, for example at the anterior axillary line, the midaxillary line, or in the posterior axillary line. The canister 414 may also be placed still more posterior beneath the lattisimus dorsi, using a reported method in Kondo et al., "Successful Intermuscular Implantation Of Subcutaneous Implantable Cardioverter Defibrillator In A Japanese Patient With Pectus Excavatum." Journal of Arrhythmia, 2016, 10.1016.

In the illustration, a suture sleeve is shown at 416 and is used to fixate the lead 410, for example, to the subcutaneous fascia. For placement, the right ITV 400 is accessed similar to the left ITV 158 as described above with respect to FIG. 5, and a tunnel is established between the left axilla and the access location such as along a portion of the inframammary crease. The lead 410 may, in this case, be relatively stiff to assist in keeping it emplaced in the patient as shown, if desired. Various designs are shown herein for the lead as well, including tines, hooks, curvature or bias of the lead, and inflatable or expandable structures. In the example of FIG. 7, a left axillary canister location is shown; a right sided, pectoral or subclavicular left or right position may be used instead, in combination with the right ITV placement 400 or, alternatively a left ITV placement.

Figure 14:
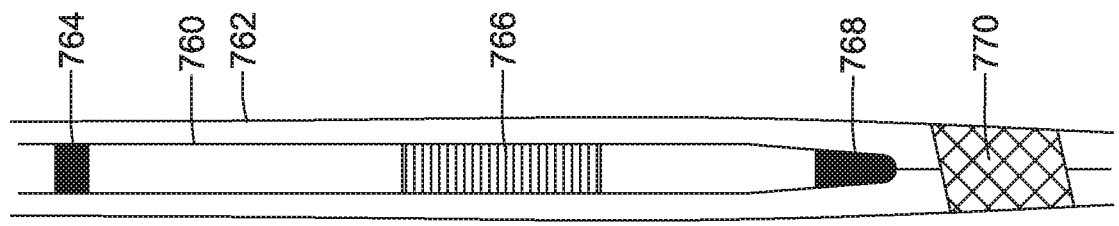
Figure 15:
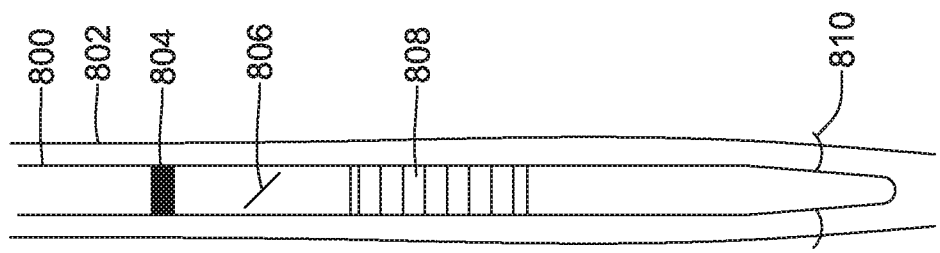

During implantation, a sheath may be provided over the lead 410, or at least a portion thereof, to retain or restrain a fixation apparatus or shape for the flexible lead, such as a 2 or 3 dimensional curvature (see FIGS. 9-10), tines (see FIG. 13), an expandable member (see FIG. 14), or hooks or a side-extending engagement structure (see FIG. 15). A stylet may be placed through the lead 410, or a portion thereof, to retain a straight shape during implantation; upon removal of the stylet, a curvature (see FIGS. 9-10) may then be released for securing the lead 410 in place.

The lead 410 may include additional or different electrodes than those shown. For example, another coil electrode may be placed on a more proximal portion of the lead 410 to reside along the inframammary crease in a location between the canister 414 and the point of access into the right costal vein 116. The additional coil at this location may be used for defibrillation, pacing, or other therapy purposes, or for sensing. If desired, second or more leads may also be placed.

FIG. 8A shows implantation from both the right coastal vein 116 and left coastal vein 118 into both ITV. In this example, the right ITV 450 is shown with the electrode structure 452 on a distal end of a lead 454 disposed therein.

A suture sleeve 456 secures the lead 454. The lead 454 includes a second branch that enters the left ITV 460 with a distal electrode structure 462 disposed therein. A second suture sleeve 466 optionally secures the lead 454 at a second location. A canister for the system is shown implanted in the left axilla. As noted above, the point of access to each of the right and left intercostal veins 116, 118, in order to enter the right and left ITV 450, 460, may be placed close to a costal groove of an inferior portion of the rib.

FIG. 8B shows an illustrative lead that may be used in the implantation configuration of FIG. 8A. The illustrative lead 500 includes a proximal plug structure shown at 502, with a split at 510, from which a shorter branch having an electrode structure 504 extends, and a longer branch 508 continuing in the axial direction to another electrode structure 506. The design is illustrative and not intended to be limiting. In another example, two separate leads may be used, rather than one integrated lead.

As shown, each electrode structure 504, 506 includes a coil electrode flanked with two sensing electrodes; other combinations of electrodes may be used. Each electrode may be electrically connected to a single contact on the plug 502 or, if desired, subsets of electrodes may be ganged together relative to a single contact on the plug 502. The distal portion may include a fixation apparatus or shape for the flexible lead, such as a 2 or 3 dimensional curve (see FIGS. 9-10), tines (see FIG. 11), an expandable member (see FIG. 14), or hooks or a side-extending engagement structure (see FIG. 15).

In any of the above examples, additional lead placement may take place. For example, an additional lead may be placed subcutaneously, within the heart, or in a different blood vessel such as the azygos vein. Additional device placement may occur as well, including, for example, the placement of a leadless cardiac pacemaker in one or more chambers of the heart.

The above examples facilitate a number of therapy options. For example, defibrillation therapy may be delivered in various configurations such as, without limitation:

Between a left ITV electrode or combination of electrodes and a right ITV electrode or combination of electrodes;
  Between a left ITV electrode and a device housing placed in the left axilla or left subclavicular location;
  Between a right ITV electrode and a device housing placed in the left axilla or left subclavicular location;
  Between a left ITV electrode and a device housing placed in the right axilla or right subclavicular location;
  Between left and right ITV electrodes electrically in common and a right or left axillary or subclavicular canister.
  Between one ITV electrode and a second ITV electrode in common with a device canister in the left or right axilla or subclavicular location
  Between a first electrode on a lead, and a second electrode on the same lead, where the first and second electrodes are in the same ITV
  Between a first electrode on a lead, and a second electrode on the same lead, where the first electrode is in an ITV, and the second electrode is in a tunnel leading to access to the ITV, such as in the inframammary crease on lead 410 in FIG. 7
  Between a first electrode in ITV and second electrode in anterior intercostal vein
  Between a first electrode in ITV and a second electrode in the posterior intercostal vein
  Between a first electrode in ITV and a second electrode in azygos vein, the hemiazygos vein, and/or the accessory hemiazygos vein
  Any one of these combinations with or without the canister of the system as an active electrode
  In any of these examples, either (or any one of the) electrode may serve as anode or cathode during therapy delivery.

In these examples, a "left ITV electrode" or "right ITV electrode" may include a single coil electrode or a combination of plural coils and/or one or more coils with one or more ring electrodes electrically in common. The above combinations may also be used for delivery of a bradycardia pacing therapy or an anti-tachyarrhythmia pacing therapy. In addition, because the left ITV lies over the interventricular septum, the above combinations may also be used for right ventricle (RV) pacing for either anti-tachycardia pacing and/or chronic atrial tachyarrhythmias. Furthermore, using the right ITV, the above combinations may also be used for right atrium (RA) pacing or p-wave sensing for timing purposes and p-wave detection to support, for example, pacing in the presence of a total block and/or cardiac resynchronization pacing by the device itself or if the device is cooperative with, for example, a leadless cardiac pacemaker. In any of the examples using an ITV electrode, the lead on which the ITV electrode resides may be placed by accessing the ITV using an intercostal vein as shown above.

Further examples may provide a resynchronization therapy by delivering pacing pulses in various configurations, such as, without limitation:

In bipolar fashion within the left ITV to pace the left ventricle, and also in bipolar fashion within the right ITV to pace the right ventricle, with relative timing between the two sets of pacing therapies determined according to analysis of cardiac output or electrical response.
  In bipolar fashion within one of the left or right ITV to stimulate a respective left or right ventricle in response to atrial sensed signals sensed with electrodes placed in an ITV at a superior location level with the atria.
  In monopolar fashion between a device housing and one or both of left or right ITV electrodes, using for timing information atrial signals sensed using additional electrodes in at least one ITV and/or far-field sensed morphology detected using a device housing.

In an example, a heart failure or resynchronization therapy may be delivered as follows, with reference to FIG. 7. A pacing therapy may be delivered by sensing atrial activity using the distal two ring electrodes shown in the electrode assembly 412 to determine timing for pace therapy delivery using the proximal coil electrode and canister 414. Numerous other combinations may be had as can be seen to those skilled in the art.

FIGS. 9-17 illustrate various lead designs. These leads may be manufactured of any suitable material and by any suitable manner. For example, numerous polymers are known for lead manufacture. Internal longitudinal or lateral support members, such as braids, core wires, etc. may be provided. Extrusion or molding may be used. Internal conductors may be formed of any suitable material (stainless steel, titanium, gold, silver, or any other conductive material may be used) and may take any suitable form, such as simple wires, coated wires, braided or wound wires, drawn wires, and/or drawn filled tubes, or other structures. The leads may include on all or a portion thereof various coatings such as an anti-microbial coating to reduce the likelihood, severity, and/or progression of infection. Some illustrative lists for such design details follow later in the disclosure.

Figure 9:
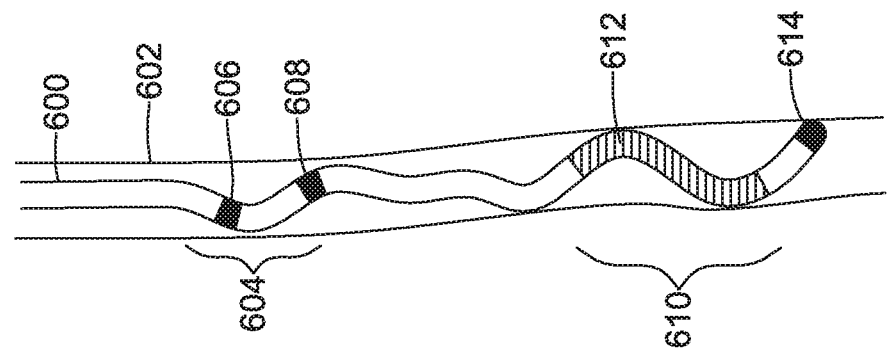

FIG. 9 shows an illustrative lead structure. A lead 600 is shown within a blood vessel 602, which may be an ITV. The lead may include ring electrodes illustrated at 606, 608, and a tip electrode 614, as well as a coil electrode at 612. Regions of curvature area shown at 604, and at 610. A single curvature may be provided instead. The curvature may be two-dimensional or three-dimensional. A two dimensional curvature may take the form, generally, of a zig-zag design, for example. Several embodiments may use a three dimensional curvature such as a pigtail or helix, for example.

In one example, the distal tip 614 is implanted inferior relative to the rest of the lead, such that the coil 612 is adjacent or level with the patient's ventricles. In another example, the distal tip is implanted superior relative to the rest of the lead, such that the coil 612 is adjacent or level with the patient's atria. In another example, the position of coil 612 is switched with the position of ring electrode 608, such that if implanted with the tip 614 superior relative to the rest of the lead, the tip 614 would be at about the level of the atria (or higher), while the coil 612 would be adjacent to or level with the ventricles.

Figure 10:
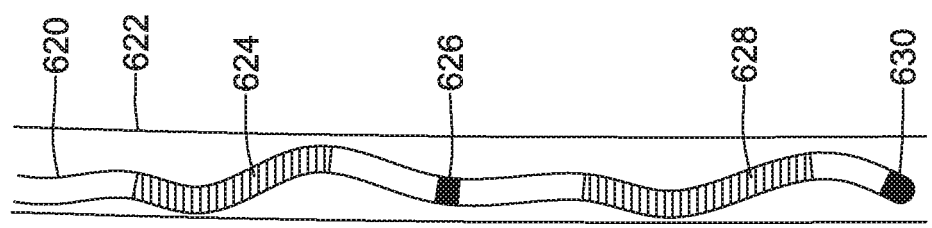

FIG. 10 shows another example. A lead 620 is shown within a blood vessel 622, which may be an ITV. The lead may include ring electrode 626 and a tip electrode 630, as well as coil electrodes 624, 628. An additional ring electrode may be placed proximal of the coil electrode 624, as shown above in FIG. 5, if desired. With this example, the coils 624 may be spaced and positioned such that one is level with the ventricles and the other is level with the atria when implanted with the tip 630 either superior or inferior. As with FIG. 9, FIG. 10 shows that the lead has several areas of curvature.

In FIGS. 9 and 10, the curvature may be assumed by the lead in several ways. In an example, the lead includes a shape memory material and is generally straight and flexible until implanted in the body; after a few minutes to warm up, the shape memory material assumes the shape shown. In another example, a stylet is placed inside the lead during implantation to retain a generally straight shape, and the lead assumes the curved shape shown when the stylet is removed. In another example, an outer sheath is used to retain the lead until it is implanted with removal of the outer sheath allowing the lead to assume a desired shape. Combinations may be used as well; for example, a lead may include a shape memory portion or material or support structure, and may be implanted with the aid of a stylet and outer sheath to retain a low profile for implantation and then, once released by removal of the stylet and sheath, the shape memory material exerts forces to assume the shapes shown. Though not shown, curvature may be used for secure placement of any of the leads shown in FIGS. 11-17, if desired.

Figure 11:
FIGS. 9-17 illustrate various lead designs.

FIG. 11 shows another example. Here, a lead 650 is shown inside a blood vessel 652, which may be the ITV. First and second ring electrodes are shown at 654, 656, and third and fourth ring electrodes are shown at 658, 660. Tines for fixation are shown at 662. The ring electrodes may be placed such that if the tines 662 are superior relative to the rest of the lead, electrodes 658, 660 would be level with the atria, and electrodes 654, 656 would be level with the ventricles. This may facilitate separate atrial and ventricular sensing and/or pacing channels. A coil electrode may also be provided.

In one example, a lead as shown in FIG. 11 is implanted in the left ITV while a separate lead is implanted in the right ITV, with the right ITV comprising a defibrillation coil electrode, with an active canister defibrillator implanted in the left axilla. This approach would allow sensing (and optionally, pacing) directly over the heart using the ring electrodes 654, 656, 658, 660, with defibrillation delivered across the majority of the myocardium between the right-sided coil electrode and the left sided canister.

Figure 12:
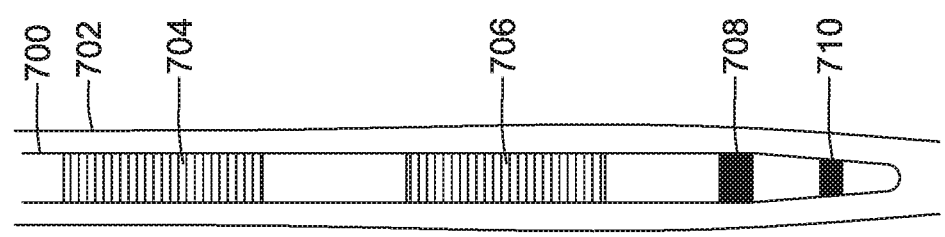

FIG. 12 shows another example. Here a lead 700 is implanted in a blood vessel 702 which may be an ITV. A first coil is shown at 704 and a second coil is shown at 706, with two distally located ring electrodes. If desired, the lead may taper as shown, though a fully cylindrical lead may be used instead. The taper may be useful during implantation to facilitate easier access through venous valves, particularly for insertions from superior to inferior, where the direction of insertion is counter to blood flow and hence valve structure. Curves or tines may be added, as well as other fixation features noted herein.

Figure 13:
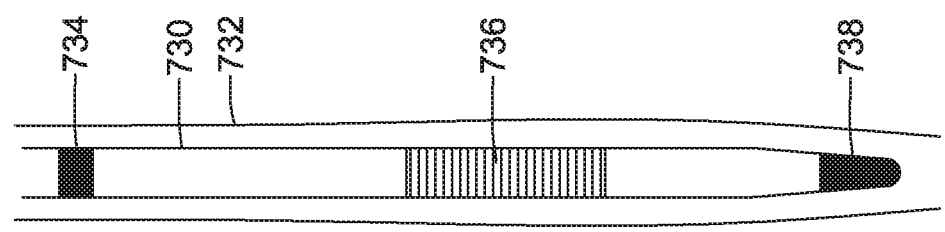

FIG. 13 shows another example. In this example, a lead 730 is shown inside of a blood vessel 732 which may be an ITV. A proximal ring electrode is shown at 734 and a coil at 736, with a distal tip electrode at 738. Curvature or tines may be added, as well as other fixation features noted herein.

FIG. 14 shows another example. Here, the lead is much as in FIG. 14, with lead 760 shown inside a blood vessel 762 which may be a ITV, and with a proximal ring electrode 764, coil electrode 766, and distal tip electrode 768. However, now, an expandable member, such as a stent 770 is shown distal to the distal tip electrode 768. For example, a self-expanding stent 770 may be provided and carried within the distal tip electrode 768 until a desired position is reached for the stent 770. Such positioning may be determined using, for example, fluoroscopy. The proximal end of the lead may include a release mechanism, such as a control wire that can be advanced relative to the lead body, to push the stent 770 beyond the distal tip electrode 768 where it can then release. Self-expanding stents are well known in the art and may include, for example, spring-like structures. The stent 770 may include coatings designed to prevent thrombus from forming thereon and/or to encourage angiogenesis to best engage the venous wall. For removal, the connection to the stent 770 may be cut, for example, to leave the stent 770 in place as the rest of the lead is removed. Optionally the stent may be later removed using, for example, a stent retriever.

FIG. 15 shows another example. Here, a lead 800 is shown in a blood vessel 802 which may be an ITV. A proximal coil electrode is shown at 804. Distal of the proximal coil electrode (though any suitable location, more proximal or more distal, may be chosen), a side-engaging member is shown at 806. For example, engaging member 806 may be an arm, coil, hook, or tine that expands outward when actuated from the proximal end of the lead. Once the lead is in a desired position, engaging member 806 may be actuated to secure the lead in place.

The lead 800 is also shown with a coil electrode at 808. Finally, at the distal tip of the lead, a plurality of hooks are shown for engaging the walls of the blood vessel 802. The engaging member 806 or hooks 810 may be coated as desired for anti-thrombogenic or pro-angiogenic reasons, for example.

Figure 16:
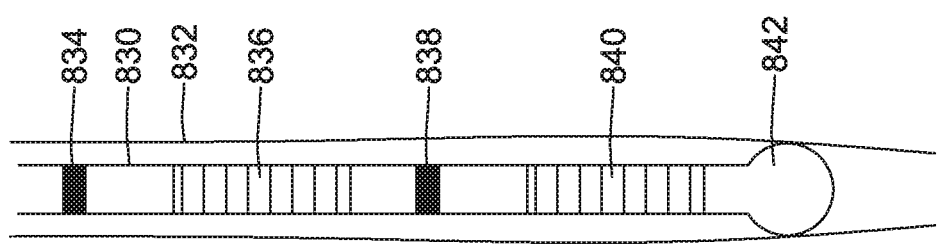

FIG. 16 shows another example. Here, a lead 830 is shown inside of a blood vessel 832 which may be an ITV. A plurality of electrodes are shown including a ring electrode 834, coil electrode 836, ring electrode 838, and coil electrode 840. At the distal end of the lead is an expandable member, such as a balloon, which may be inflated to secure the lead in place. It should be noted that the ITV is a blood vessel which, if occluded, will not necessarily cause harm to the patient as contralateral accommodation occurs readily. The balloon 842 may be expanded using inflation pressure, for example. A compliant or non-compliant material may be used the balloon. Rather than a balloon, an expandable sponge-type member that increases in volume once sufficiently wetted may be used instead.

Figure 17:
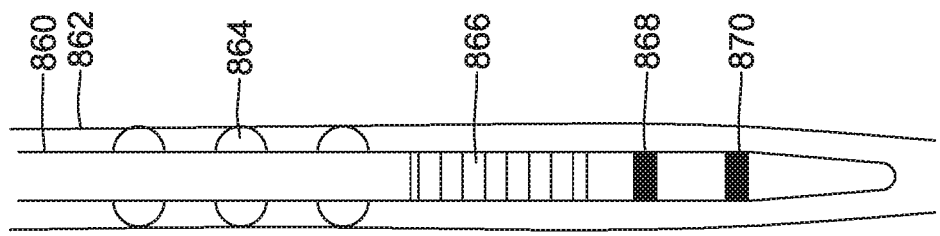

FIG. 17 shows another example. In this example, the lead 860 is shown in a blood vessel 862 which may be an ITV. This example includes a plurality of lobes 864 which hold the lead 860 in place inside the blood vessel 862. For example, the lobes may self-expand on removal of an outer delivery sheath or catheter, or the lobes may be expanded by movement of an outer shell of the lead relative to an inner shell. A coil electrode is shown at 866 and ring electrodes are shown at 868, 870.

The examples of FIGS. 9-17 are merely illustrative. Some examples may omit any fixation on the portion of the lead that extends into the blood vessel, and may instead rely on fixation using a suture sleeve subcutaneously placed as shown in certain of the above examples. In some examples, a relatively stiff lead may be used, as repeated flexion is not necessary when implanted in the ITV in the same manner as is the case inside the heart. A stiff lead is believed to be less likely to migrate.

FIGS. 18A-18D show an illustrative ITV shock coil lead structure 900. In some cases, intercostal veins may be a potential access route for the ITV shock coil lead structure 900. However, intercostal veins may have a diameter on the order of 1 mm or less, whereas the ITV may have a diameter on the order of 3 mm or greater. Accordingly, in various embodiments, the shock coil structure 900 may be configured to have a delivery configuration with a diameter that allows the coil structure 900 to travel through the intercostal vein to the ITV without damaging the intercostal vein. The coil structure 900 may then access the ITV through an ostium and the coil structure 900 may be advanced through the ITV to a desired location. Once placed at the desired location, the coil structure 900 may be configured to deploy into an expanded configuration that has a larger diameter relative to the diameter of the coil structure 900 in its delivery configuration. In some cases, the expanded configuration may provide tissue contact with the ITV as well as lead fixation.

In some cases, the shock coil structure 900 may be configured to travel through the intercostal vein to the azygos vein, the hemiazygos vein, or the accessory hemiazygos vein without damaging the intercostal vein. The coil structure 900 may then be advanced into the azygos vein, the hemiazygos vein, or the accessory hemiazygos vein through an ostium and the coil structure 900 may be advanced through the azygos vein, the hemiazygos vein, or the accessory hemiazygos vein to a desired location. Once placed at the desired location, the coil structure 900 may be configured to deploy into an expanded configuration that has a larger diameter relative to the diameter of the coil structure 900 in its delivery configuration. In some cases, the expanded configuration may provide tissue contact with the azygos vein, the hemiazygos vein, or the accessory hemiazygos vein, as well as lead fixation.

FIG. 18A is a side view of the coil structure 900 in the delivery configuration and FIG. 18B is a cross-sectional front view of the coil structure 900 in the delivery configuration. As shown, the coil structure 900 may include a shock coil 902, a lead body 904, an inner coil 906, and a delivery stylet 908. According to various embodiments, the delivery stylet 908 may be inserted into a cavity of the inner coil 906 and advanced through the coil structure 900. In some cases, the delivery stylet 908 may straighten the coil structure 900 into its delivery configuration. Once the coil structure 900 is in its delivery configuration, the intercostal vein may be accessed using the Seldinger technique or another venipuncture or cut-down technique.

As mentioned above, the inner diameter of the intercostal vein may be on the order of 1 mm or less. Accordingly, in various embodiments, the delivery configuration of the coil structure 900 may have an outer diameter less than the inner diameter of the intercostal vein, allowing the coil structure 900 to be inserted and advanced through the intercostal vein without damaging the tissue of the intercostal vein (e.g., scraping, puncturing, tearing, etc.). The coil structure 900 may then enter the ITV, the azygos vein, the hemiazygos vein, or the accessory hemiazygos vein through the ostium. Depending on the chosen intercostal vein, in some cases, the coil structure 900 may be advanced through the ITV, the azygos vein, the hemiazygos vein, or the accessory hemiazygos vein in a superior direction to a desired location. In other cases, the coil structure 900 may be advanced through the ITV, the azygos vein, the hemiazygos vein, or the accessory hemiazygos vein in an inferior direction to the desired location.

Figure 18C:
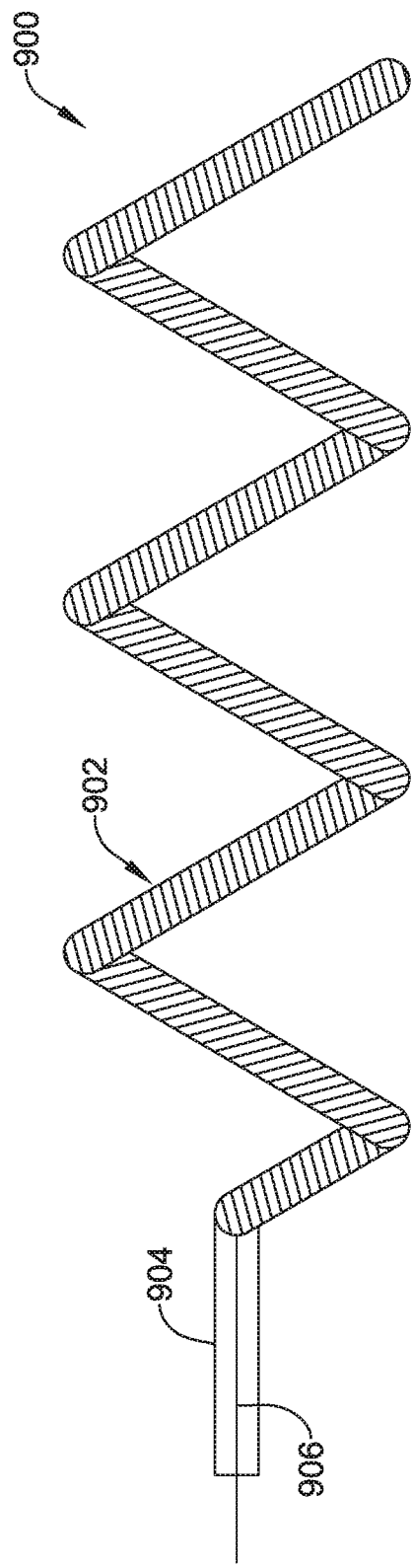
Figure 18D:
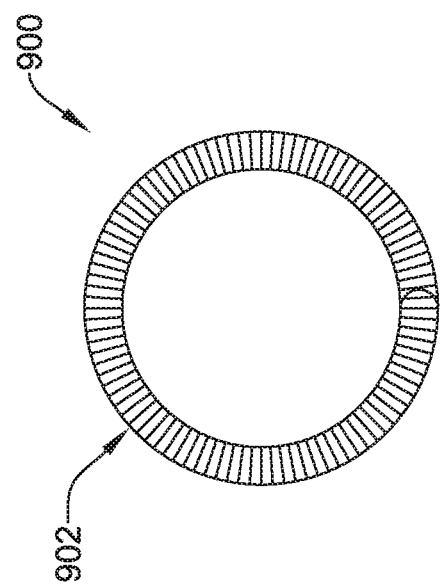

FIG. 18C is a side view of the coil structure 900 in the expanded configuration and FIG. 18D is a cross-sectional front view of the coil structure 900 in the expanded configuration. As mentioned above, the inner diameter of the ITV may be on the order of 3 mm or more. Accordingly, in various embodiments, once the coil structure 900 is in the desired position in the ITV, the delivery stylet 908 may be removed or retracted from the inner cavity of the inner coil 906. In other cases, once the coil structure 900 is in the desired position in the azygos vein, the hemiazygos vein, or the accessory hemiazygos vein, the delivery stylet 908 may be removed or retracted from the inner cavity of the inner coil 906. In some cases, the coil structure 900 may recoil or open up into a helical or spiral expanded configuration. In some cases, when in its expanded configuration, the coil structure 900 may have a larger outer diameter (e.g., on the order of >3 mm) than in its delivery configuration, allowing the shock coil 902 to make tissue contact with the ITV as well as fixation of the lead body 904 to the ITV. In other cases, the expanded configuration may allow the shock coil 902 to make tissue contact with the azygos vein, the hemiazygos vein, or the accessory hemiazygos vein as well as fixation of the lead body 904 to the azygos vein, the hemiazygos vein, or the accessory hemiazygos vein. Furthermore, in certain embodiments, the surface area of the coil structure 900 in its expanded configuration may allow for shorter coil lengths of the shock coil 902 and/or help facilitate integrated electrodes throughout the shock coil.

Figure 19:
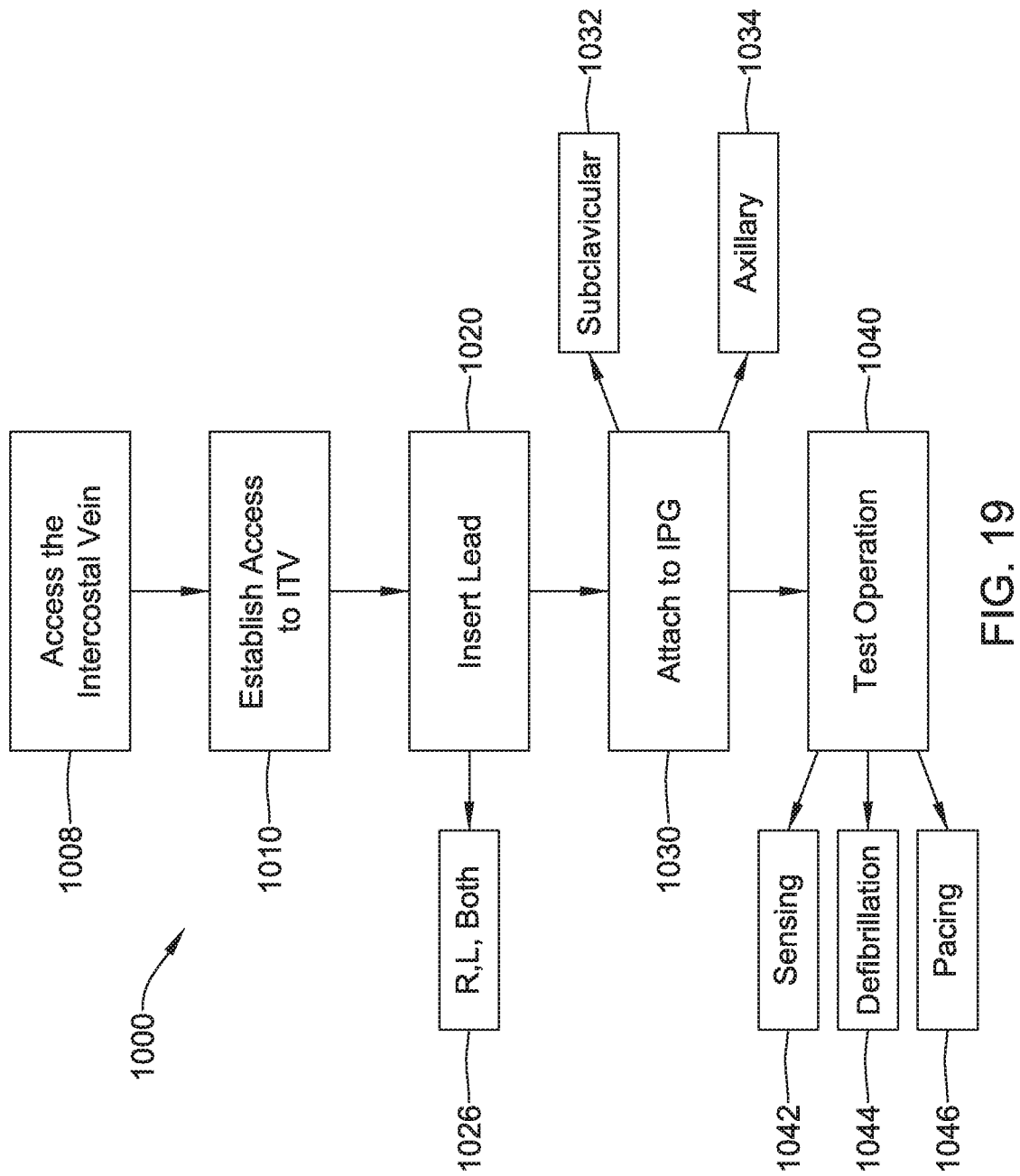
FIG. 19 is a block flow diagram for an illustrative method.

FIG. 19 is a block flow diagram for an illustrative method for providing a cardiac stimulus system to a patient. As shown at 1000, the method comprises accessing the intercostal vein 1008, then establishing access to the ITV 1010, inserting a lead in the ITV 1020, attaching an IPG to the lead 1030, and performing test operations 1040.

Accessing the intercostal vein in a costal groove on the inferior portion of the rib may be achieved by the examples described with respect to FIGS. 4-8. Establishing access to the ITV 1010 may include entering the intercostal vein and passing superiorly therefrom into the ITV. In another example, rather than, or in addition to, accessing the ITV in block 1010, the posterior of the patient may be accessed by passage through an intercostal vein (which may be the same intercostal vein for both anterior and posterior positioning/ lead advancement). Posterior access may include placement of a device residing in a selected posterior intercostal vein, and/or access to one or more of the azygos vein, the hemiazygos vein, or the accessory hemiazygos vein.

In an example, inserting a lead 1020 may include insertion superiorly 1022, such as by starting in the intercostal vein and advancing the lead in a superior direction into the ITV. The right ITV, left ITV, or both ITV vessels may be accessed, as indicated at 1026.

Other vessels and implanted lead locations may also be used (such as having a lead in the azygos vein, an intracardiac lead, a subcutaneous lead) or additional devices such as a separately implanted leadless cardiac pacemaker may be included as well. In a further example, one or more of the transverse veins that flow into the ITV may be used for placement of an electrode or lead. For example, upon accessing an ITV, a physician may further access and emplace a lead or electrode into one of the anterior intercostal veins which run along the intercostal spaces of the anterior chest.

In an example, attaching to an IPG may include attaching to a canister located in a subclavicular location 1032, historically a common place to put an implanted canister for a transvenous defibrillator or pacemaker. In another example, attaching to an IPG may include attaching to a canister located in an axillary position 1034, such as that used with the S-ICD System. Other IPG locations may be used. Attachment may be directly to the IPG or to a splitter, yoke, or lead extension, if desired.

In an example, test operation 1040 may be used to verify one or both of device functionality and efficacy. For example, sensing operations 1042 may be tested and configured to check for adequate signal availability, for example, or by setting gain, filtering, or sensing vector selection parameters. Defibrillation operations 1044 may be tested by inducting an arrhythmia such as a ventricular fibrillation to determine whether the device will sense the arrhythmia and, if the arrhythmia is sensed, to ensure that the device can adequately provide therapy output by delivering defibrillation at a preset energy. Defibrillation testing 1044 may include determining for a given patient an appropriate defibrillation threshold, and setting a parameter for therapy delivery at some safety margin above the defibrillation threshold.

Prior transvenous systems would typically deliver up to 35 Joules of energy at most, with storage of up to 40 Joules of energy, using peak voltages in the range of up to nearly 1000 volts. The original S-ICD System can deliver up to 80 Joules of energy, with 65 Joules often used for in-clinic system testing, with a peak voltage in the range of 1500 volts. The ITV location may facilitate energy levels similar to those of traditional transvenous systems (5-35 Joules, approximately), or may be somewhat higher (5 to about 50 joules, for example), or may still be higher (10 to about 60 joules, for example). Pacing thresholds may also be closer to those for traditional transvenous systems than the more recent S-ICD System.

In an example, pacing testing operation 1046 may include determining which, if any, available pacing vectors are effective to provide pacing capture. If desired, parameters may be tested as well to determine and optimize settings for delivery of cardiac resynchronization therapy. This may include testing of pacing thresholds to optimize energy usage and delivery, as well as checking that adverse secondary effects, such as patient sensation of the delivered pacing or inadvertent stimulation of the phrenic nerve, diaphragm or skeletal muscles are avoided.

Some embodiments of the present invention may take the form of an implantation tool set configured for use in implanting a cardiac device, such as a lead, into an ITV. Some such embodiments may include an introducer sheath. Some such embodiments may include a guide catheter. Some such embodiments may include a guidewire. Some such embodiments may further include a tool set for performing a Seldinger technique to access a blood vessel percutaneously.

Some embodiments of the present invention take the form of an implantable cardiac stimulus device comprising a lead and an implantable canister for coupling to the lead, the implantable canister housing operational circuitry configured to deliver output therapy in the form of at least one of bradycardia pacing, anti-tachycardia pacing, cardiac resynchronization therapy, or defibrillation, using a lead implanted in an ITV and a canister implanted in a patient.

As used herein, a coil electrode may be a helically wound element, filament, or strand and may include multiple such filaments/strands/elements. The filament forming the coil may have a generally round or a generally flat (e.g. rectangular) cross-sectional shape, as desired. However, other cross-sectional shapes may be used. The coil electrode may have a closed pitch, or in other words, adjacent windings may contact one another. Alternatively, the coil electrode may have an open pitch such that adjacent windings are spaced a distance from one another. The pitch may be uniform or varied along a length of the coil electrode. A varied pitch may be gradual tapered changes in pitch or abrupt or step-wise changes in pitch.

A coil electrode may have a length L that is generally larger than a width W. Round, oval or flattened coil electrodes may be used. Coil electrodes may have a length in the range of one to ten centimeters. In an example, a coil having a six or eight centimeter length may be used. In another example, a lead may have two four centimeter coils. Coils and leads may be in the range of four to ten French, or larger or smaller, in outer profile.

Coils and leads may be coated. For example, a thin permeable membrane may be positioned over a shock coil or other electrode and/or other portions of the lead to inhibit or to promote tissue ingrowth. Coatings, such as, but not limited to expanded polytetrafluoroethylene (ePTFE) may also be applied to the coil and/or lead to facilitate extraction and/or to reduce tissue ingrowth. In some embodiments, one or more of the electrodes, whether coils, rings, or segmented electrodes, include a high capacitive coating such as, but not limited to iridium oxide (IrOx), titanium nitride (TiN), or other "fractal" coatings which may be used, for example, to improve electrical performance. Steroidal and antimicrobial coatings may be provided as well.

The various components of the devices/systems disclosed herein may include a metal, metal alloy, polymer, a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS:

N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers for use in the leads discussed above may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS A), polycarbonates, ionomers, biocompatible polymers, other suitable materials, or mixtures, combinations, copolymers thereof, polymer/metal composites, and the like.

In at least some embodiments, portions or all of the accessory devices and their related components may be doped with, made of, or otherwise include a radiopaque material. Radiopaque materials are understood to be materials capable of producing a relatively bright image on a fluoroscopy screen or another imaging technique during a medical procedure. This relatively bright image aids the user of the accessory devices and their related components in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the accessory devices and their related components to achieve the same result.

Any guidewire, introducer sheath, and/or guide catheter design suitable for medical interventions may be used for accessing the venous structures discussed herein.

The implantable systems shown above may include an implantable pulse generator (IPG) adapted for use in a cardiac therapy system. The IPG may include a hermetically sealed canister that houses the operational circuitry of the system. The operational circuitry may include various elements such as a battery, and one or more of low-power and high-power circuitry. Low-power circuitry may be used for sensing cardiac signals including filtering, amplifying and digitizing sensed data. Low-power circuitry may also be used for certain cardiac therapy outputs such as pacing output, as well as an annunciator, such as a beeper or buzzer, telemetry circuitry for RF, conducted or inductive communication (or, alternatively, infrared, sonic and/or cellular) for use with to a non-implanted programmer or communicator. The operational circuitry may also comprise memory and logic circuitry that will typically couple with one another via a control module which may include a controller or processor. High power circuitry such as high power capacitors, a charger, and an output circuit such as an H-bridge having high power switches may also be provided for delivering, for example, defibrillation therapy. Other circuitry and actuators may be included such as an accelerometer or thermistor to detected changes in patient position or temperature for various purposes, output actuators for delivering a therapeutic substance such as a drug, insulin or insulin replacement, for example.

Some illustrative examples for hardware, leads and the like for implantable defibrillators may be found in commercially available systems such as the Boston Scientific Teligen™ ICD and Emblem S-ICD™ System, Medtronic Concerto™ and Virtuoso™ systems, and St. Jude Medical Promote™ RF and Current™ RF systems, as well as the leads provided for use with such systems.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various to combinations or permutations. The scope of the invention should be determined with reference to the appended claims, along with the full scope of equivalents to which such claims are entitled.

The claimed invention is:

1. A method of implanting a lead for use in a cardiac stimulus system in a patient, the lead having at least one electrode thereon, the lead also having a proximal end for coupling to an implantable canister and a distal end; the method comprising:
   inserting the distal end of the lead into an intercostal vein;
   advancing the distal end of the lead from the intercostal vein into an internal thoracic vein (ITV) and to a desired location relative to the heart of the patient.

2. The method of claim 1, further comprising establishing access to the intercostal vein by making an incision at a costal groove on an inferior portion of a rib, inserting an introducer sheath into the intercostal vein; and advancing at least the distal end of the lead through the introducer sheath.

3. The method of claim 1, further comprising establishing access to the intercostal vein by use of the Seldinger technique.

4. The method of claim 1 further comprising:
   inserting a needle through the skin and into the intercostal vein; and
   advancing a sheath into the intercostal vein; and
   advancing the distal end of the lead through the sheath.

5. The method of claim 1, further comprising establishing access to the intercostal vein using ultrasound guidance.

6. The method of claim 1 further comprising establishing access to the intercostal vein using a cut down procedure to expose the intercostal vein.

7. The method of claim 1 wherein the intercostal vein is a left anterior intercostal vein.

8. The method of claim 1 wherein the intercostal vein is a right anterior intercostal vein.

9. The method of claim 1 wherein the step of advancing the distal end of the lead from the intercostal vein into the ITV and to a desired location relative to the heart of the patient comprises advancing the distal end of the lead in a superior direction within the ITV.

10. The method of claim 1 wherein the step of advancing the distal end of the lead from the intercostal vein into the ITV and to a desired location relative to the heart of the patient comprises advancing the distal end of the lead in an inferior direction within the ITV.

11. The method of claim 1 further comprising accessing the intercostal vein at a first location, creating a subcutaneous tunnel between the first location and a second location, placing the lead through the subcutaneous tunnel, connecting the lead to the implantable canister for the system, and implanting the canister at the second location.

12. The method of claim 1 further comprising placing a stylet in the lead to hold the lead in a first, lower profile configuration and, after placement of the lead at the desired location, removing the stylet to release the lead into an expanded configuration relative to the first configuration, thereby anchoring the lead.

13. The method of claim 12 wherein the first configuration is generally straight, and the second configuration is in the form of a spiral.

14. The method of claim 1, wherein the lead further includes a second electrode thereon and the step of advancing the distal end from the intercostal vein into the ITV and to a desired location relative to the heart of the patient is performed such that the second electrode remains in the intercostal vein.

15. The method of claim 1 further comprising:
   making an incision for implantation of the canister to couple to the lead;
   accessing the intercostal vein through the incision;
   dissecting a pocket to receive the canister;
   connecting the canister to the lead; and
   implanting the canister in the pocket.

16. The method of claim 15 wherein the incision is located at approximately the left axilla of the patient.

17. The method of claim 15 wherein the incision is located at approximately the right axilla of the patient.

18. The method of claim 15 wherein the at least one electrode on the lead includes at least a first electrode, and the canister either includes a second electrode thereon or is configured as a second electrode, the method further comprising, after placing both the canister and the lead, delivering an electrical therapy between the first and second electrodes.

19. The method of claim 18 wherein the electrical therapy is configured for pacing the patient's heart.

20. The method of claim 18 wherein the electrical therapy is configured for defibrillating the patient's heart.

* * * * *